US012640240B2

(12) United States Patent
Adhikari et al.

(10) Patent No.: US 12,640,240 B2
(45) Date of Patent: May 26, 2026

(54) SINGLE SIGN-ON CLINICAL TRIAL MANAGEMENT PLATFORM

(71) Applicant: IQVIA Inc., Parsippany, NJ (US)

(72) Inventors: Aruna Thapa Adhikari, Natick, MA (US); Gregory Paul Friedman, Raleigh, NC (US); Peter Nadudvari, London (GB); Naouel Baili Benabdallah, Parsippany, NJ (US); Sakti Singh, Parsippany, NJ (US); Meredith Leigh Malloy, Parsippany, NJ (US); Devi Chandrasekaran, Parsippany, NJ (US); Ioannis Kalantzis, London (GB)

(73) Assignee: IQVIA Inc., Parsippany, NJ (US)

( * ) Notice: Subject to any disclaimer, the term of this patent is extended or adjusted under 35 U.S.C. 154(b) by 13 days.

(21) Appl. No.: 18/431,623

(22) Filed: Feb. 2, 2024

(65) Prior Publication Data

US 2024/0266010 A1     Aug. 8, 2024

Related U.S. Application Data

(60) Provisional application No. 63/443,329, filed on Feb. 3, 2023.

(51) Int. Cl.
*H04L 9/40* (2022.01)
*G16H 10/20* (2018.01)

(52) U.S. Cl.
CPC ......... *G16H 10/20* (2018.01); *H04L 63/0815* (2013.01); *H04L 63/105* (2013.01)

(58) Field of Classification Search
CPC .... G16H 10/20; H04L 63/0815; H04L 63/105
See application file for complete search history.

(56) References Cited

U.S. PATENT DOCUMENTS

| | | | |
|---|---|---|---|
| 11,790,107 B1 | 10/2023 | Jain et al. | |
| 2011/0313782 A1 * | 12/2011 | DeMeyer | G06Q 10/06 705/2 |

(Continued)

OTHER PUBLICATIONS

Drain et al., "Global migration of clinical research during the era of trial registration," PLoS One, Feb. 28, 2018, 13(2):1-13.

(Continued)

*Primary Examiner* — Gil H. Lee
(74) *Attorney, Agent, or Firm* — ALG Intellectual Property, LLC

(57) ABSTRACT
A method includes ingesting, by a clinical trial management platform, data from multiple clinical trial site systems associated with multiple clinical trials, responsive to authentication of user credentials of a user, providing the user with access to the clinical trial management platform, based on the user credentials, identifying a particular clinical trial associated with the user, through the clinical trial management platform, providing the user with access to multiple clinical trial software services based on the authenticated user credentials, based on the ingested data for the particular clinical trial associated with the user, presenting to the user a user-specific task list for user tasks related to the particular clinical trial; and through the clinical trial management platform, establishing a communication link between the user and another user, the communication link enabling direct, real-time messaging via the clinical trial management platform between the user and the other user.

27 Claims, 25 Drawing Sheets

(56)　　　　　　　References Cited

U.S. PATENT DOCUMENTS

| | | | |
|---|---|---|---|
| 2014/0222444 A1 | 8/2014 | Cerello et al. | |
| 2015/0254432 A1 | 9/2015 | Stumm et al. | |
| 2015/0286802 A1 | 10/2015 | Kansara | |
| 2017/0228501 A1* | 8/2017 | Turner, Jr. | G06Q 30/0277 |
| 2019/0026849 A1 | 1/2019 | DeMeyer et al. | |
| 2019/0206520 A1 | 7/2019 | Eteminan et al. | |
| 2022/0036373 A1* | 2/2022 | O'Brien | G06Q 50/18 |
| 2022/0215908 A1 | 7/2022 | Padmos et al. | |
| 2024/0029901 A1* | 1/2024 | Ezhov | G16H 10/60 |
| 2024/0242792 A1* | 7/2024 | Lake | G16H 10/20 |

OTHER PUBLICATIONS

International Search Report and Written Opinion in International Appln. No. PCT/US2024/014327, mailed on Apr. 17, 2024, 10 pages.

* cited by examiner

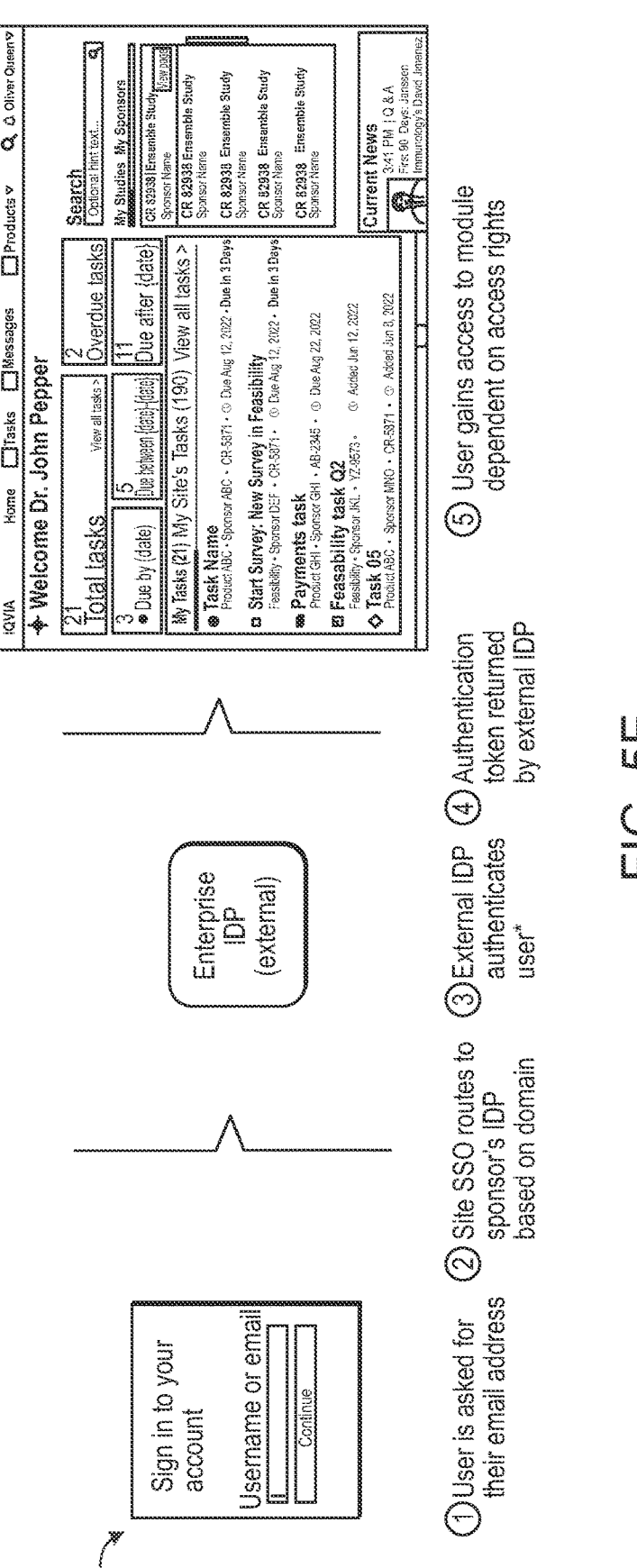

Sign in to your account

Username or email

Continue

① User is asked for their email address

② Site SSO routes to sponsor's IDP based on domain

Enterprise IDP (external)

③ External IDP authenticates user*

④ Authentication token returned by external IDP

⑤ User gains access to module dependent on access rights iQVIA     Home    Tasks    Messages    Products ⌄    Q    Oliver Queen ⌄

✦ Welcome Dr. John Pepper

21
Total tasks                    View all tasks >

2
Overdue tasks

3
• Due by (date)

5
Due between (date)-(date)

11
Due after (date)

My Tasks (21) My Site's Tasks (190)  View all tasks >

⊛ Task Name
Product ABC • Sponsor ABC • CR-5871 •  ⊙ Due Aug 12, 2022 • Due in 3 Days ☐ Start Survey. New Survey in Feasibility
Feasibility • Sponsor DEF • CR-5871 •   ⊙ Due Aug 12, 2022 • Due in 3 Days ⊞ Payments task
Product GHI • Sponsor GHI • AB-2345 •  ⊙  ⊙ Due Aug 22, 2022

☑ Feasibility task Q2
Feasibility • Sponsor JKL • YZ-8573 •   ⊙ Added Jun 12, 2022

◇ Task 05
Product ABC • Sponsor MNO • CR-5871 •  ⊙ Added Jun 3, 2022

Search
Optional hint text...    Q

My Studies  My Sponsors
CR 82938 | Ensemble Study    View page >
Sponsor Name

CR 82938  Ensemble Study
Sponsor Name

CR 82938  Ensemble Study
Sponsor Name

CR 82938   Ensemble Study
Sponsor Name

Current News
3:41 PM | Q & A
First 90 Days: Janssen
Immunology's David Jimenez

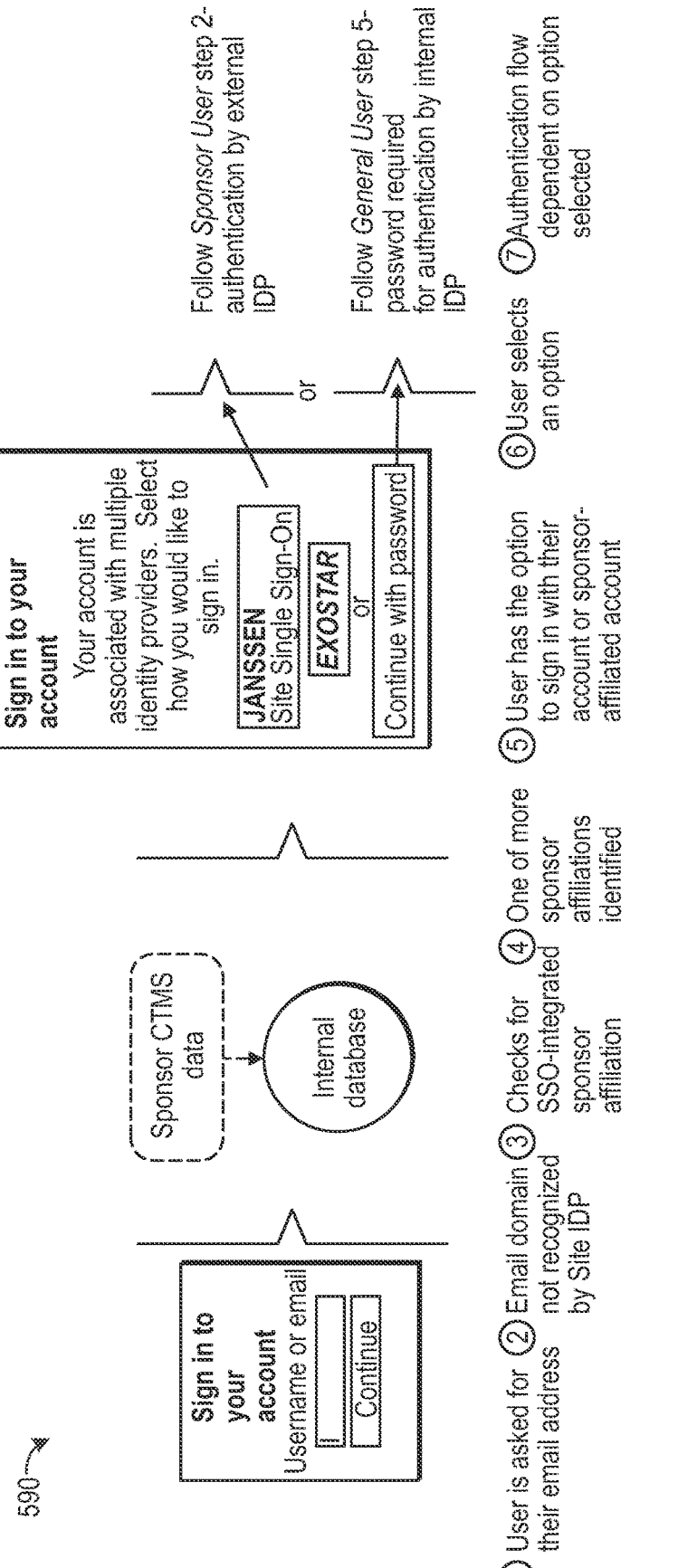

590

① User is asked for their email address
② Email domain not recognized by Site IDP
③ Checks for SSO-integrated sponsor affiliation
④ One of more sponsor affiliations identified
⑤ User has the option to sign in with their account or sponsor-affiliated account
⑥ User selects an option
⑦ Authentication flow dependent on option selected Follow *Sponsor User* step 2-authentication by external IDP Follow *General User* step 5-password required for authentication by internal IDP

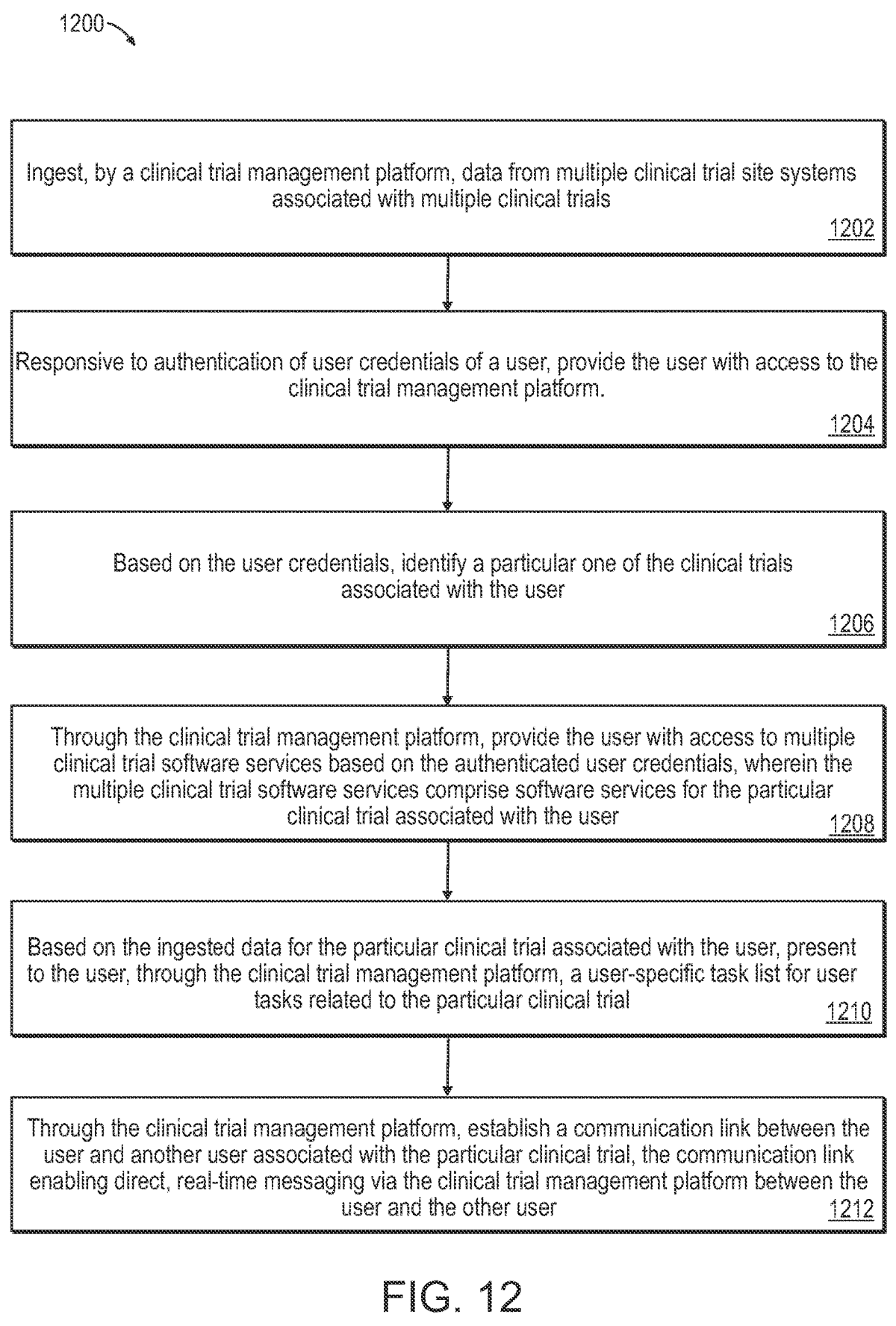

Ingest, by a clinical trial management platform, data from multiple clinical trial site systems associated with multiple clinical trials

1202

Responsive to authentication of user credentials of a user, provide the user with access to the clinical trial management platform.

1204

Based on the user credentials, identify a particular one of the clinical trials associated with the user

1206

Through the clinical trial management platform, provide the user with access to multiple clinical trial software services based on the authenticated user credentials, wherein the multiple clinical trial software services comprise software services for the particular clinical trial associated with the user          1208

Based on the ingested data for the particular clinical trial associated with the user, present to the user, through the clinical trial management platform, a user-specific task list for user tasks related to the particular clinical trial          1210

Through the clinical trial management platform, establish a communication link between the user and another user associated with the particular clinical trial, the communication link enabling direct, real-time messaging via the clinical trial management platform between the user and the other user          1212

FIG. 12

SINGLE SIGN-ON CLINICAL TRIAL MANAGEMENT PLATFORM

CROSS-REFERENCE TO RELATED APPLICATIONS

This application claims priority to and the benefit of U.S. Provisional Patent Application No. 63/443,329, filed Feb. 3, 2023, the entire contents of which is hereby incorporated by reference in its entirety.

TECHNICAL FIELD

The present disclosure relates to a management platform for clinical trials and studies.

BACKGROUND

Clinical trials and other types of studies involve many individuals along with the exchange of considerable information. Individuals taking part the trials, studies, and other types of events can include patients, healthcare professionals, and trial managers, among others. Along with information for executing the trials and studies, other types of information may be exchanged such a communications among these many individuals (e.g., planning information, site selection information, and information regarding tasks to be executed). Such communications may utilize multiple communications systems that may not operate efficiently with one another and can delay the exchange of information to the involved individuals, thereby hindering the trials and other types of studies.

SUMMARY

The present disclosure relates to an innovative clinical trial management platform designed to streamline the process for clinical trials and other studies. This platform acts as a centralized hub where site (e.g., clinical trial site) and study staff can access multiple applications through a single login, greatly reducing the complexity of managing numerous URLs and login credentials. The platform integrates various internal and external applications, thereby providing users with a plethora of tools to support the clinical trial process. The platform efficiently ingests and transforms data from these applications and standardizes the ingested data to create a unified user experience. The platform also enhances task management through comprehensive dashboards that leverage artificial intelligence (AI), thereby enabling users to prioritize and organize their tasks efficiently. Moreover, the platform facilitates real-time or near-real-time communication between sponsors, contract research organizations (CROs), and site users, both individually and in groups, providing essential tools for study conduct. Through these and other aspects, the platform described here simplifies and optimizes the management and execution of clinical trials and other studies, offering a more cohesive and efficient workflow for all involved parties and reducing the amount resources needed to complete a clinical study.

In general, in a first aspect, a method includes: ingesting, by a clinical trial management platform, data from multiple clinical trial site systems associated with multiple clinical trials; responsive to authentication of user credentials of a user, providing the user with access to the clinical trial management platform; based on the user credentials, identifying a particular one of the clinical trials associated with the user; through the clinical trial management platform, providing the user with access to multiple clinical trial software services based on the authenticated user credentials, in which the multiple clinical trial software services include software services for the particular clinical trial associated with the user; based on the ingested data for the particular clinical trial associated with the user, presenting to the user, through the clinical trial management platform, a user-specific task list for user tasks related to the particular clinical trial; and through the clinical trial management platform, establishing a communication link between the user and another user associated with the particular clinical trial, the communication link enabling direct, real-time messaging via the clinical trial management platform between the user and the other user.

In general, in a second aspect combinable with the first aspect, operations of the method include: presenting, to a user, a single sign-on interface for the clinical trial management platform; receiving the user credentials through the single sign-on interface; and authenticating the received user credentials.

In general, in a third aspect combinable with the first or second aspects, the user credentials include user credentials for a federated enterprise system, and the operations of the method include receiving an indication of authentication of the user credentials from the federated enterprise system.

In general, in a fourth aspect combinable with any of the first through third aspects, providing the user access to the multiple clinical trial software services includes allowing the user to access the multiple clinical trial software services without re-entering the user credentials.

In general, in a fifth aspect combinable with any of the first through fourth aspects, at least one of the multiple clinical trial software services is provided by a different vendor than the other clinical trial software services.

In general, in a sixth aspect combinable with any of the first through fifth aspects, the multiple clinical trial software services include one or more of: a clinical trial investigator site portal, a clinical trial safety module, a clinical trial consent module, a clinical trial financial module.

In general, in a seventh aspect combinable with any of the first through sixth aspects, operations of the method include identifying the clinical trial software services to which to provide access based on a role of the user in the clinical trial.

In general, in an eighth aspect combinable with any of the first through seventh aspects, operations of the method include using a predictive model, processing the ingested data based on the role of the user to provide a user-specific recommendation or alert.

In general, in a ninth aspect combinable with any of the first through eighth aspects, ingesting the data includes ingesting one or more of site activation data, site engagement data, training data, feasibility data, safety data, profile data, or payment data.

In general, in a tenth aspect combinable with any of the first through ninth aspects, operations of the method include indexing the ingested data.

In general, in an eleventh aspect combinable with any of the first through tenth aspects, operations of the method include masking personally identifiable information (PII) or personal health information (PHI) in the ingested data.

In general, in a twelfth aspect combinable with any of the first through eleventh aspects, operations of the method include standardizing a format of the ingested data from different clinical trial site systems.

In general, in a thirteenth aspect combinable with any of the first through twelfth aspects, ingesting the data includes merging clinical and product authorization metadata.

In general, in a fourteenth aspect combinable with any of the first through thirteenth aspects, operations of the method include identifying the particular clinical trial associated with the user based on the merged clinical and product authorization metadata.

In general, in a fifteenth aspect combinable with any of the first through fourteenth aspects, operations of the method include identifying the clinical trial software services to which to provide access based on the merged clinical and product authorization metadata.

In general, in a sixteenth aspect combinable with any of the first through fifteenth aspects, operations of the method include processing the ingested data using a predictive model to identify or schedule the user tasks for the user-specific task list.

In general, in a seventeenth aspect combinable with any of the first through sixteenth aspects, operations of the method include processing data indicative of progress of the particular clinical trial using the predictive model to suggest a next task for the user.

In general, in an eighteenth aspect combinable with any of the first through seventeenth aspects, operations of the method include adjusting operation of the predictive model based on user interaction with the clinical trial management platform.

In general, in a nineteenth aspect combinable with any of the first through eighteenth aspects, operations of the method include: processing the ingested data using a predictive model; and automating one or more of the user tasks based on the processed ingested data and based on a role of the user.

In general, in a twentieth aspect combinable with any of the first through nineteenth aspects, operations of the method include using a predictive model, processing the ingested data based on a context of the data to identify or schedule one or more of the user tasks or to provide a notification to the user.

In general, in a twenty-first aspect combinable with any of the first through twentieth aspects, establishing a communication link includes establishing a chat session.

In general, in a twenty-second aspect combinable with any of the first through twenty-first aspects, establishing the chat session includes establishing a chat session among multiple users associated with the particular clinical trial.

In general, in a twenty-third aspect combinable with any of the first through twenty-second aspects, operations of the method include facilitating communication using a generative artificial intelligence (AI) tool.

In general, in a twenty-fourth aspect combinable with any of the first through twenty-third aspects, operations of the method include automatically selecting, based on metadata associated with the user, a large language model for the generative AI tool.

In general, in a twenty-fifth aspect combinable with any of the first through twenty-fourth aspects, facilitating communication includes translating or summarizing content and providing the translated or summarized content to the user.

In general, in a twenty-sixth aspect combinable with any of the first through twenty-fifth aspects, facilitating communication includes generating a suggested communication using the generative AI tool.

In an aspect, a computing system includes one or more processors coupled to a memory, the processors and memory configure to perform a method according to any of the aspects or embodiments described above.

In an aspect, a non-transitory computer readable medium stores instructions for causing a computing system to perform a method according to any of the aspects or embodiments described above.

The details of one or more implementations are set forth in the accompanying drawings and the description below. Other features and advantages will be apparent from the description and drawings, and from the claims.

BRIEF DESCRIPTION OF THE DRAWINGS

FIG. 5E illustrates an example SSO flow for a federated enterprise user.

FIG. 5G illustrates an example SSO flow for a federated site user.

FIG. 12 illustrates an example process for clinical trial management.

Like reference numbers and designations in the various drawings indicate like elements.

DETAILED DESCRIPTION

The present disclosure provides a flexible, user-friendly, and comprehensive clinical trial management platform that accommodates a wide range of tools and applications, promoting efficiency and ease of use in clinical trial management. The platform includes single sign-on, vendor-agnostic ecosystem that allows for the seamless integration of a wide array of products, applications, and capabilities, which provides users with unprecedented flexibility in tool selection and ease-of-access relative to systems that are limited to a specific set of disparate tools each having separate credentials. This integration ensures consistent data handling across various platforms, thereby increasing the accuracy and reliability of trial management and managing risk. Furthermore, the platform centralizes access and oversight into a single platform, addressing the issue of fragmentation inherent in approaches that utilize multiple systems and portals. The platform is designed with a focus on user experience, ensuring that it is lightweight and easy to navigate. Additionally, the platform's flexible and decoupled design allows users to easily adapt and customize their toolset, avoiding the constraints of monolithic systems. The platform combines task management and communication tools within its platform, which streamlines workflows and enhances coordination among trial stakeholders relative to systems that treat task management and communication as separate components. These and other aspects enable to platform to improve the outcomes for various individuals and entities associated with trials, such as patients, sites, site users, and sponsors.

Figure 1:
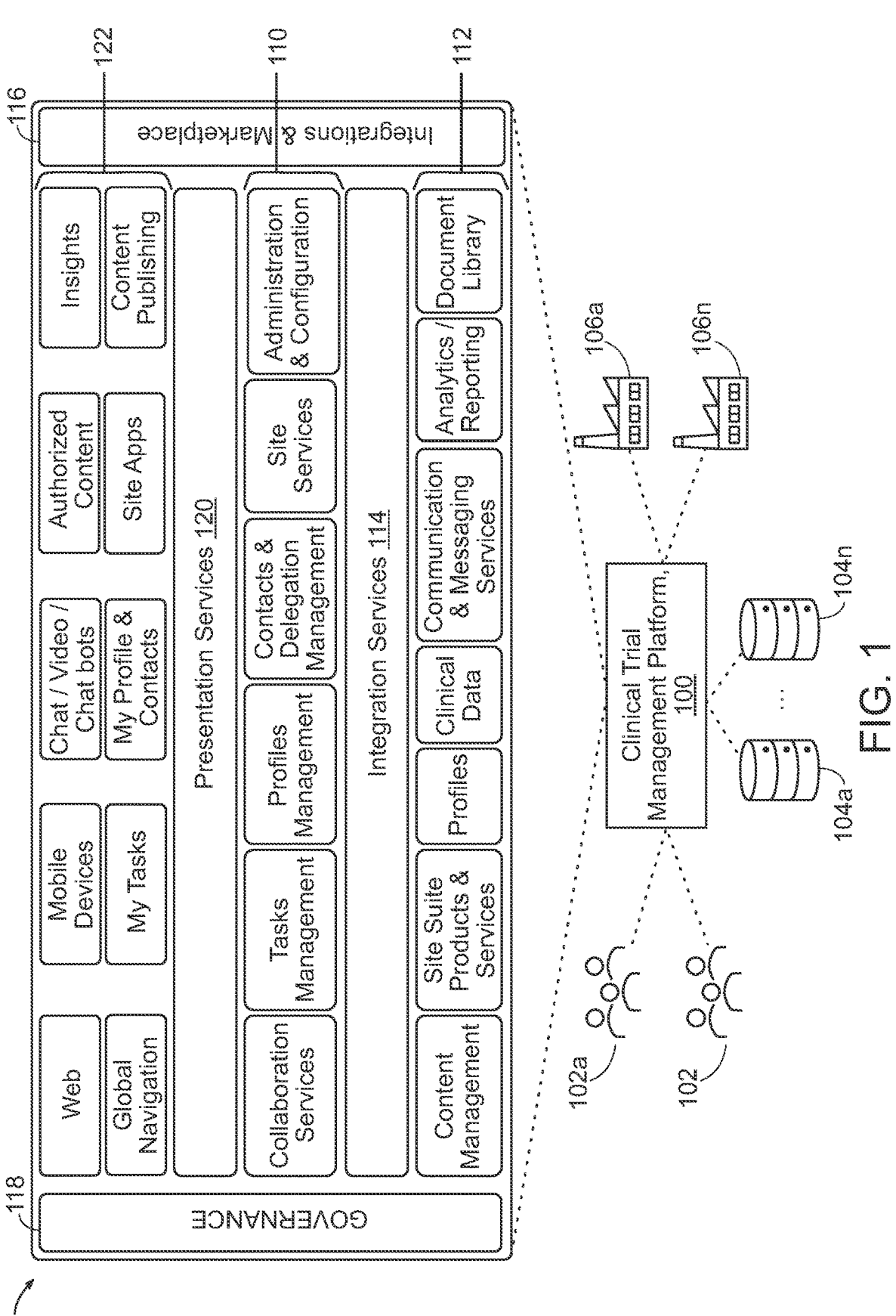
FIG. 1 illustrates an example clinical trial management platform.

Referring to FIG. 1, an example clinical trial management platform 100 is shown. The platform 100 acts as a central aggregator that seamlessly integrates multiple users 102a-102n (e.g., site users, sponsor users), systems 104a-104n (e.g., clinical trial systems, site systems), and sites 106a-106n (e.g., clinical trial sites) to facilitate management of clinical trials. A visualization 108 illustrates an example architecture employed by the platform 100. This architecture highlights the layered approach to service delivery employed by the platform 100, as well as the interaction between these layers to provide a comprehensive user experience.

In this example, the architecture includes core systems and services 110 (e.g., collaboration services, tasks management, profiles management, contacts and delegation management, site services, and administration and configuration) and supplemental systems and services 112 (e.g., content management, site suite products and services, profiles, clinical data, communication and messaging services, analytics and reporting, and document library). An integration services layer 114 serves to integrate the core and supplemental systems and services 112 (among other layers), as well as any external integrations 116. Governance services 118 are applied to standardize data ingestion, processing, and integration within the platform 100. A presentation services layer 120 enables users 102a-102n to interact with the platform 100 through various frontend applications 122 (e.g., web and/or mobile applications) that provide interfaces for navigating the platform 100, viewing tasks, managing profiles and contacts, interacting with collaboration tools (e.g., chat, video chat, chatbots, and the like), viewing insights, accessing authorized content, publishing content, and interacting with site applications. The systems and services provided by the platform 100 are described in further detail below.

Cross-Platform and Vendor-Agnostic Single Sign-On (SSO)

In general, the platform 100 addresses the fragmented login and application management experience by providing a cross-platform, vendor-agnostic SSO solution. This system unifies identity management, allowing users 102a-102n from sites, sponsors, and CROs to move between various clinical study applications without maintaining separate login credentials for each. Leveraging an intelligent authentication mechanism, the platform 100 can incorporate adaptive authentication methods that consider user behavior, location, and device security status, offering enhanced security and user convenience.

Affiliated Studies and Products Navigation

The platform 100 also enables seamless navigation between different studies and affiliated products. By aggregating user and study data, the platform 100 provides dynamic application selection based on user authorization. This creates a personalized and efficient navigation experience, and can employ machine learning (ML) and/or artificial intelligence (AI) algorithms to predict and surface the most relevant studies and tools for each user based on their history and preferences.

Unified Tasks Across Sponsors, Studies, and Products

The task management system employed by the platform 100 aggregates tasks from various sources, providing a cohesive interface with intelligent task prioritization. In some examples, the task management system leverages AI/ML algorithms to suggest the next best actions for users, integrates with calendar systems to align tasks with users' schedules, and/or pushes notifications to preferred devices, thereby enhancing the overall efficiency of clinical trial management.

Centralized Study Data

The platform 100 can centralize study data collection using a standardized canonical data model. This model serves as the foundation for harmonizing data across multiple applications, ensuring consistency and accuracy. In some examples, the platform 100 uses AI for predictive analytics and real-time data updates to improve the decision-making processes.

Cross Calendar Sharing

In some examples, the platform 100 offers a centralized calendar where users can view and manage deadlines and tasks across multiple studies. Intelligent features, such as automatic deadline adjustments based on study progress and AI-powered reminders tailored to individual users' work habits, can also be offered by the platform 100.

Centralized Engagement Tools

The platform 100 can include embedded links to engagement tools, providing SSO access to various applications and tools in a single click. In some examples, the platform 100 intelligently suggests the most relevant tools to users based on their current tasks and study phase, enhancing user engagement and efficiency.

Centralized Study Contact Management and Communications

The platform 100 can centralize contact information, enabling easy access to key study contacts and facilitating communication via a built-in chat feature. An intelligent conversational AI can further streamline communication by providing instant responses to common queries and flagging specific issues for human intervention.

Centralized Study Chat Solution

The chat solution included in the platform 100 provides real-time or near-real- time communication with the ability to maintain an auditable trail for regulatory purposes. Advanced AI capabilities can analyze conversation patterns to improve response effectiveness and regulatory compliance.

AI Chatbot for Study Guidance

The AI chatbot within the platform 100 can parse study documentation to provide instant guidance and support, reducing the redundancy of sponsor or CRO personnel responses. In some examples, advanced natural language processing is used to interpret and respond to complex queries more effectively.

Centralized Notification Service

By centralizing notifications, the platform 100 ensures that users receive timely information from one location. In some examples, intelligent notification management is used to prioritize alerts based on urgency and relevance, learning from user interactions to improve over time.

CRO and Sponsor Content Management Tools

The platform 100 offers content management tools tailored to the clinical trial industry's needs, allowing for targeted distribution of content. In some examples, AI is employed to analyze engagement data, helping to refine content creation and distribution strategies.

Cross Sponsor, Study, and Product Analytics

The analytics capabilities of the platform 100 offer insights into how site users interact with tools, providing valuable data for sponsors and CROs. The platform 100 can also use AI to derive predictive insights, improving tool adoption and user experience.

Orchestrated Document Management Access

A centralized document management system within the platform 100 allows users to access and manage regulatory documents efficiently. The platform 100 can use intelligent categorization and retrieval algorithms to streamline document management and ensure compliance.

Figure 2:
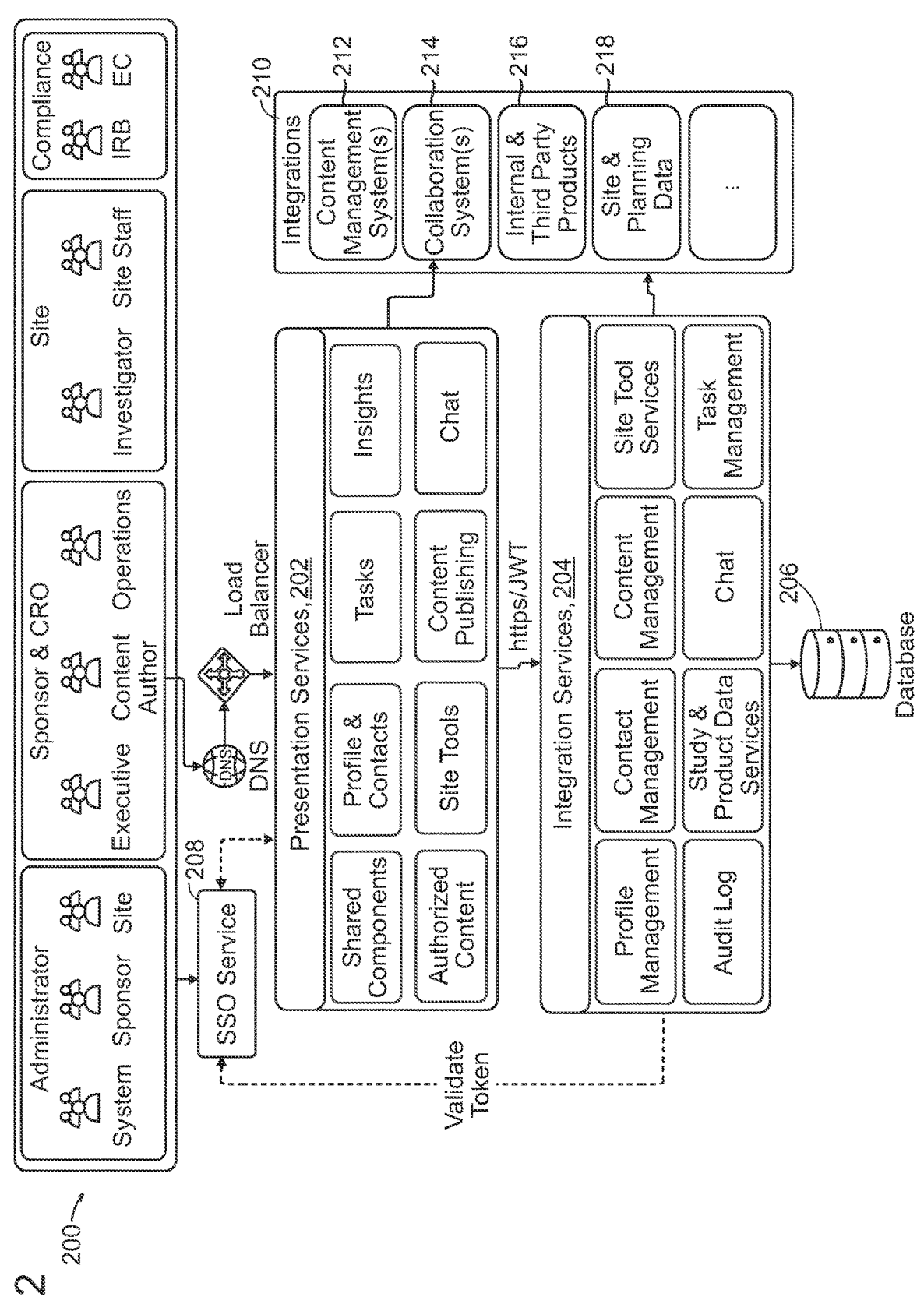
FIG. 2 illustrates an example architecture of a clinical trial management platform.

Referring to FIG. 2, an example architecture 200 of the clinical trial management platform 100 is shown. In this example, the architecture 200 is a three-tier architecture that includes a presentation services layer 202, an integration services layer 204, and a database 206. The presentation services layer 202, which can be the same as or similar to the presentation services layer 120, can include API (e.g., React API) and UI/UX components for providing various frontend applications to enable users to access the platform 100. The integration services layer, which can be the same as or similar to the integration services layer 114, can also include API (e.g., REST API, Java/Python API) components for performing the various integrations provided by the platform 100. The database 206 can store different types of data ingested by the platform.

The architecture 200 further includes an SSO service 208 for performing SSO and authentication, as described herein. The architecture 200 also includes various integrations 210, including content management systems 212 (e.g., Contentful) for content authoring, workflows, tagging, and delivery, collaboration systems 214 (e.g., Twilio for chat, Sengrid for emails), internal and external (e.g., third party) products 216 that are integrated based on, for example, the SSO and data contracts, and site and planning data 218, among others.

Figure 3A:
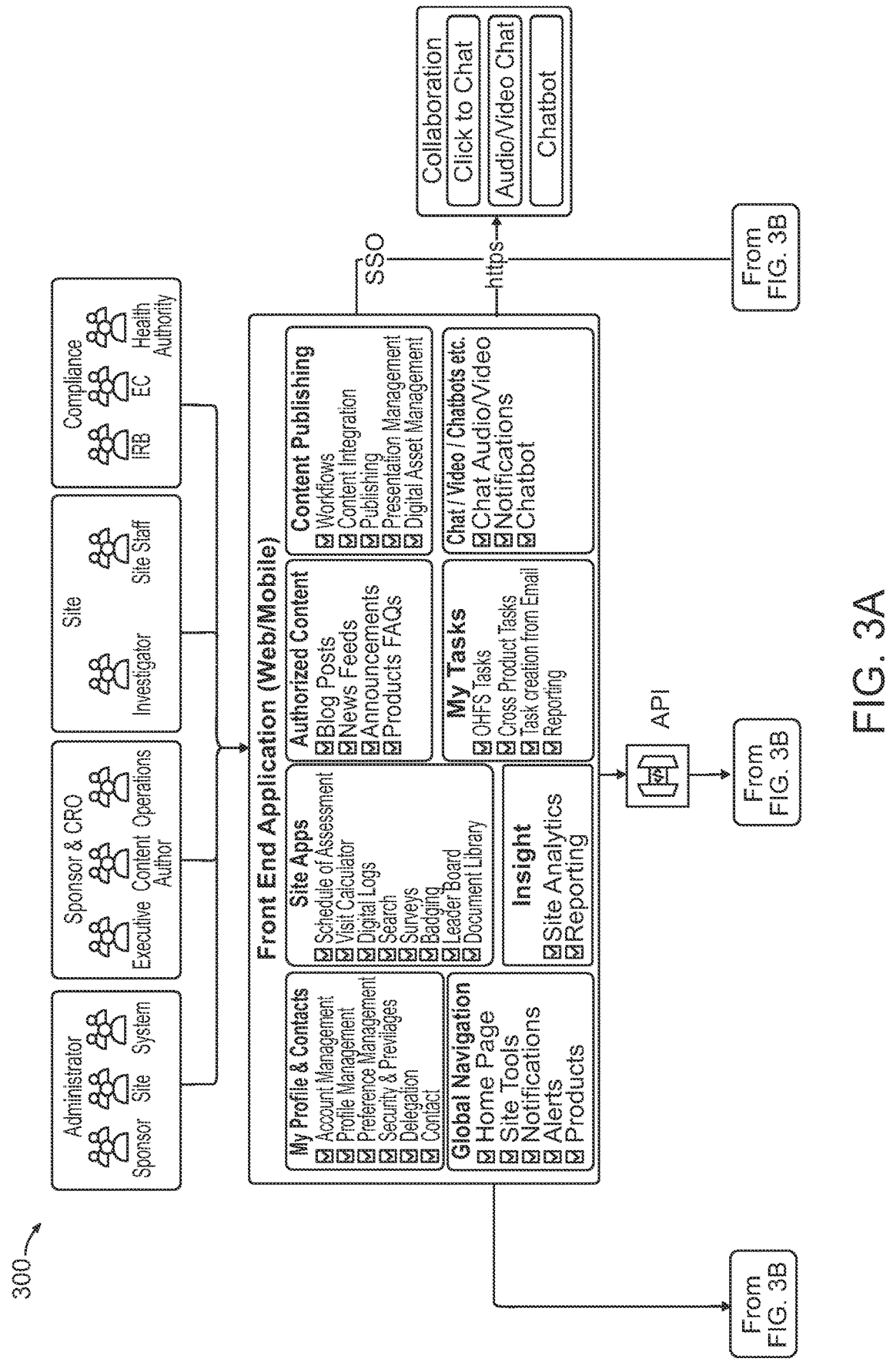
FIG. 3 illustrates an example architecture of a clinical trial management platform.
Figure 3B:
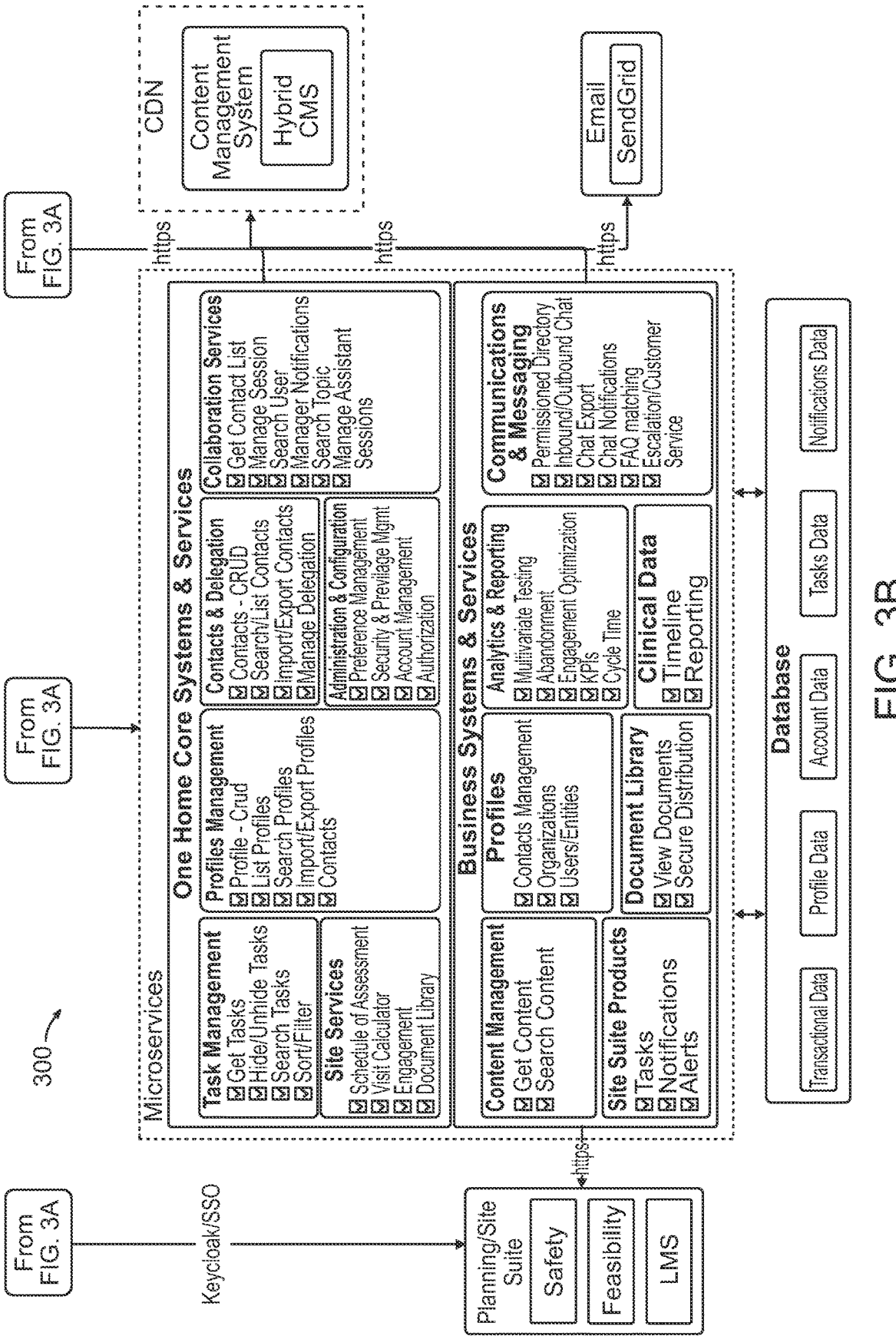

FIGS. 3A and 3B illustrate another example architecture 300 of the platform 100. The architecture 300 can be the same as or similar to the architecture 200 and the architecture shown in visualization 108, but includes additional details on the operations performed by the various components of the platform 100.

Figure 4A:
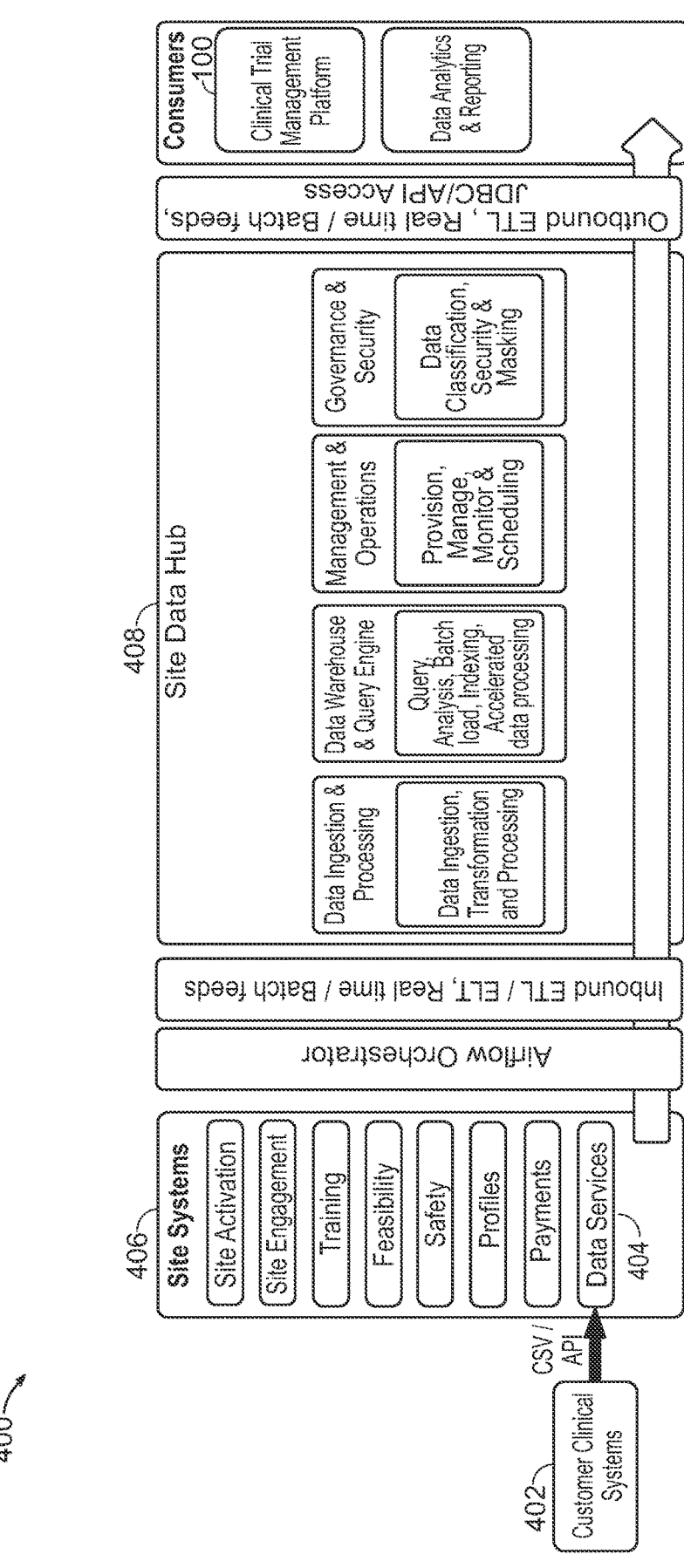
FIG. 4A illustrates a diagram of an example data integration process.

Referring to FIG. 4A, a diagram 400 depicting an example data integration process is shown. Such a process standardizes data ingestion, processing, and integration through, for example, the site and planning data hub (e.g., the site and planning data 218). In this example, clinical data 402 is ingested and curated through trial design and site engagement (TDSE) data services 404. The clinical data 402 from the TDSE data services 404 and other data from various site systems 406 is ingested and mastered in a site data hub 408. Product user mapping data (e.g., product authorization data) can also be ingested into the site data hub 408 through product specific data pipelines. Once ingested, the platform 100 (among other consumers, such as data analytics and reporting services) can pull the clinical and product data from the site data hub 408 and use it as authorization metadata and master data for clinical and product specific data entities, as described herein. The ability of the platform 100 to standardize data ingestion, processing, and integration, including the merging of clinical and product authorization metadata, allows the platform 100 to provide users with customized access to clinical trial software services and personalized tasks, among others.

Figure 4B:
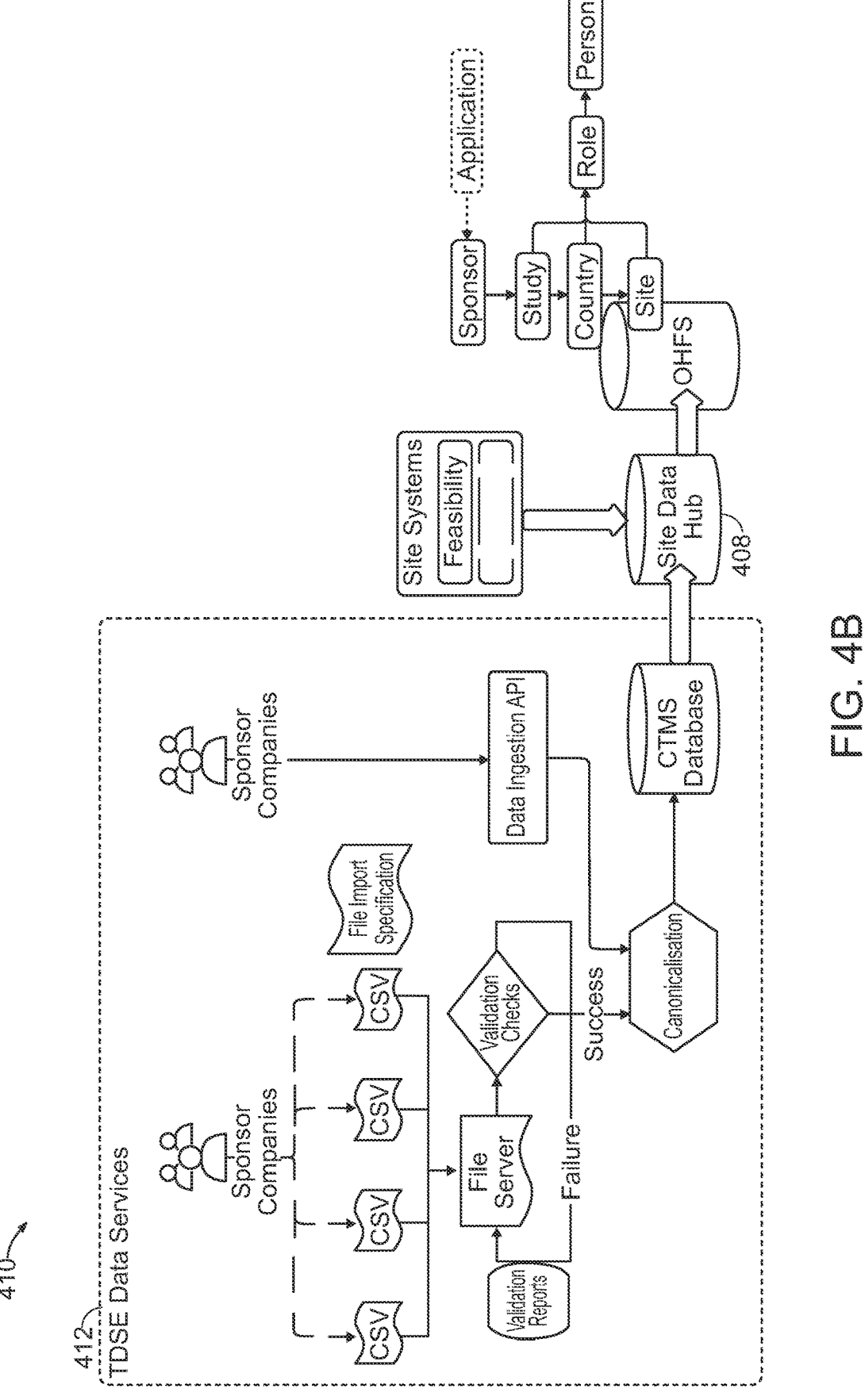
FIG. 4B illustrates a diagram of an example clinical data integration process.

FIG. 4B shows a diagram 410 depicting an example clinical data integration process. In this example, TDSE data services 412 import clinical data from various sponsors using, for example, CSV data import and API integration. Once imported, the clinical data is canonicalized 414 and stored in a clinical trial management system database 416 before being ingested into the site data hub 408 (e.g., as described with respect to FIG. 4A). The platform 100 (sometimes referred to as OHFS) can then access the clinical data from the site hub 408 and store the data for further processing. In some examples, the stored clinical data can include information about sponsors, studies and applications associated with the sponsors, countries and sites associated with the studies, and persons and roles associated with the study, site, and/or country.

Figure 4C:
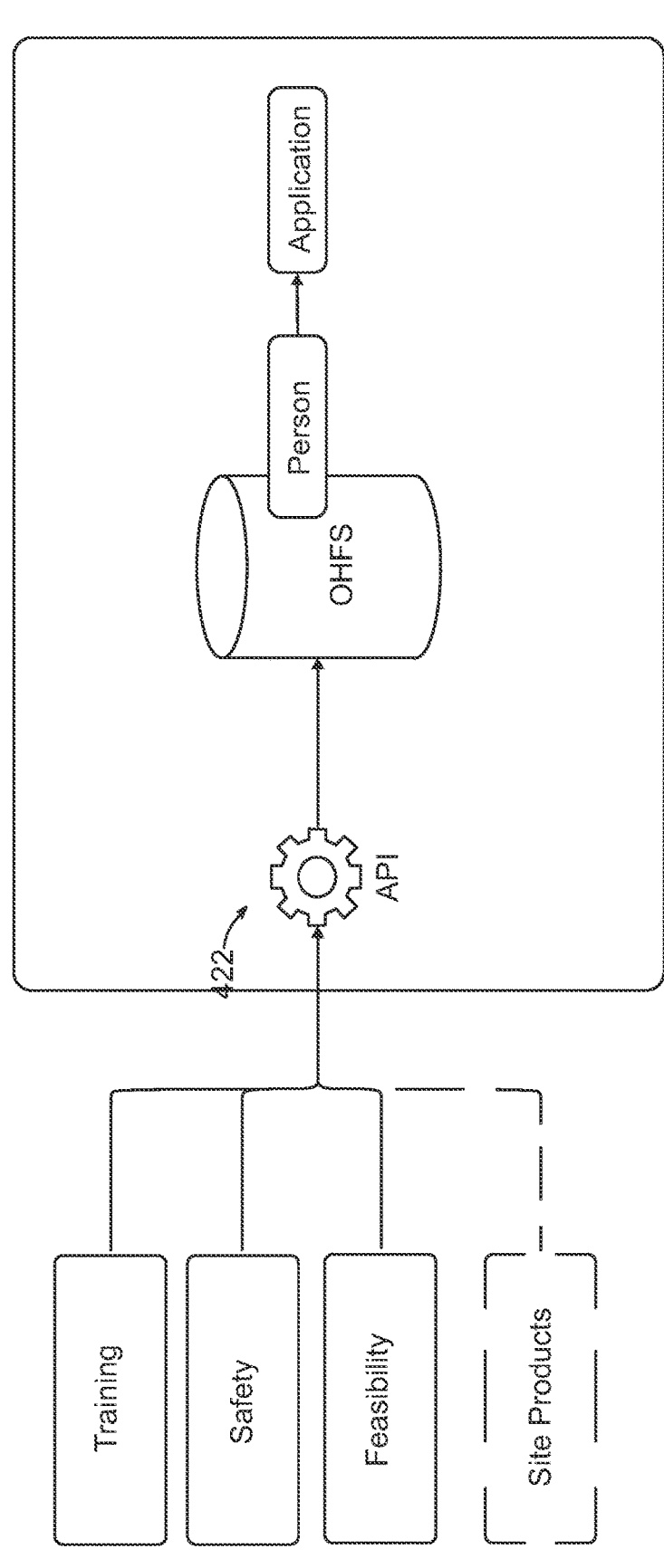
FIG. 4C illustrates a diagram of an example product authorization data integration process.

Referring to FIG. 4C, a diagram 420 illustrating an example product authorization data integration process is shown. In general, product authorization data includes data indicating whether a particular person or group of persons is authorized to use a product (e.g., an application, a software service, a software system, etc.) or particular features of a product. In this example, the platform 100 publishes an API contract and a standard API 422 for product authorization data. Then, each product that is integrated with the platform 100 can push product-to-person mapping data to the platform using the API 422. In this manner, product-specific authorization data can be ingested by the platform 100.

Figure 4D:
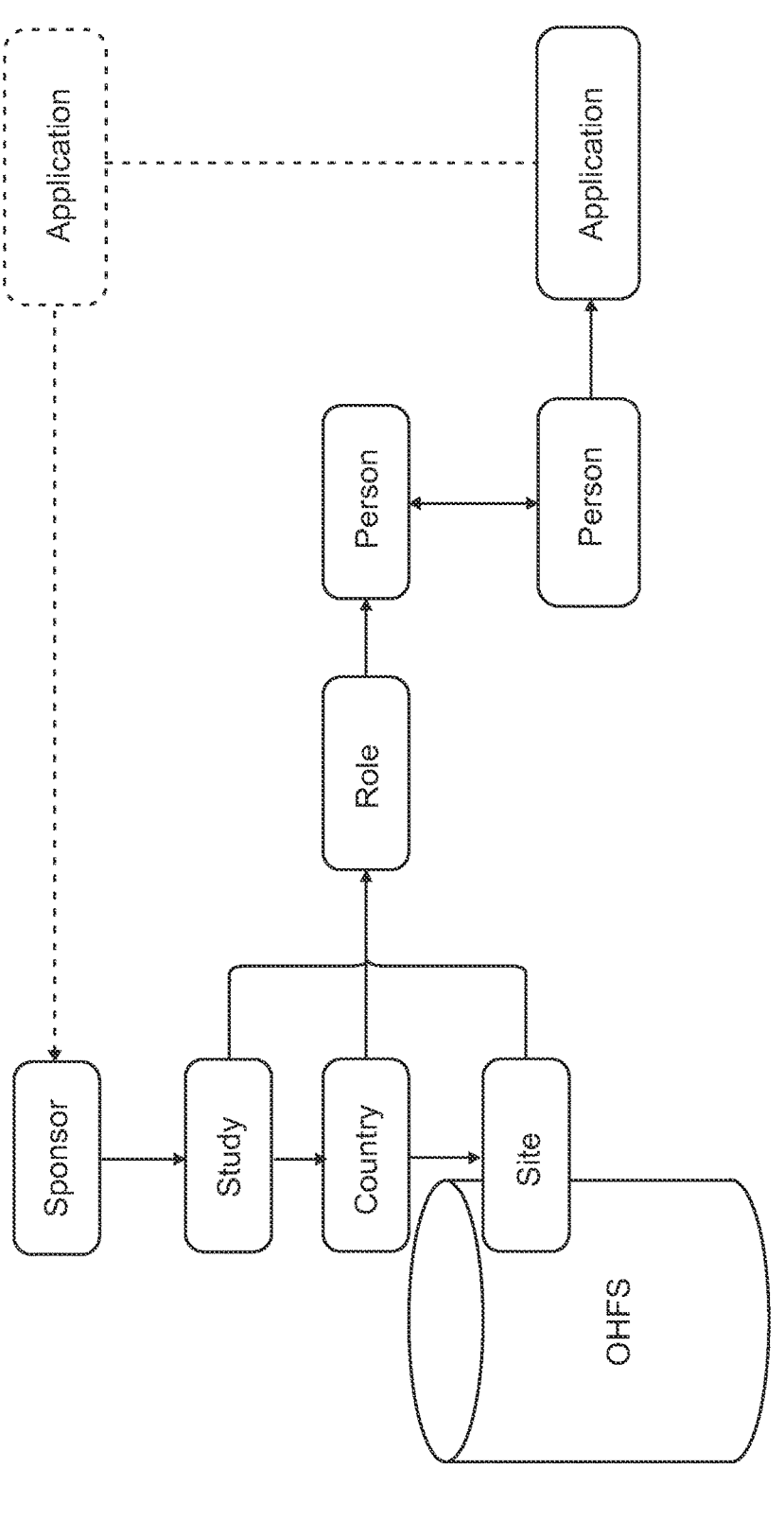
FIG. 4D illustrates a diagram of an example of merging clinical and product authorization data.

FIG. 4D shows a diagram 430 depicting the merging (or linking) of clinical and product authorization data within the platform 100. In this example, the clinical data and the product authorization metadata are merged or linked at the person level. Such a merge or link can be based on matching names or other identifiers for the person. The merged clinical and authorization metadata enables the platform to show accurate product, sponsor, study, site and other information that the particular user is entitled to access based on clinical and product data mapping.

Figure 4E:
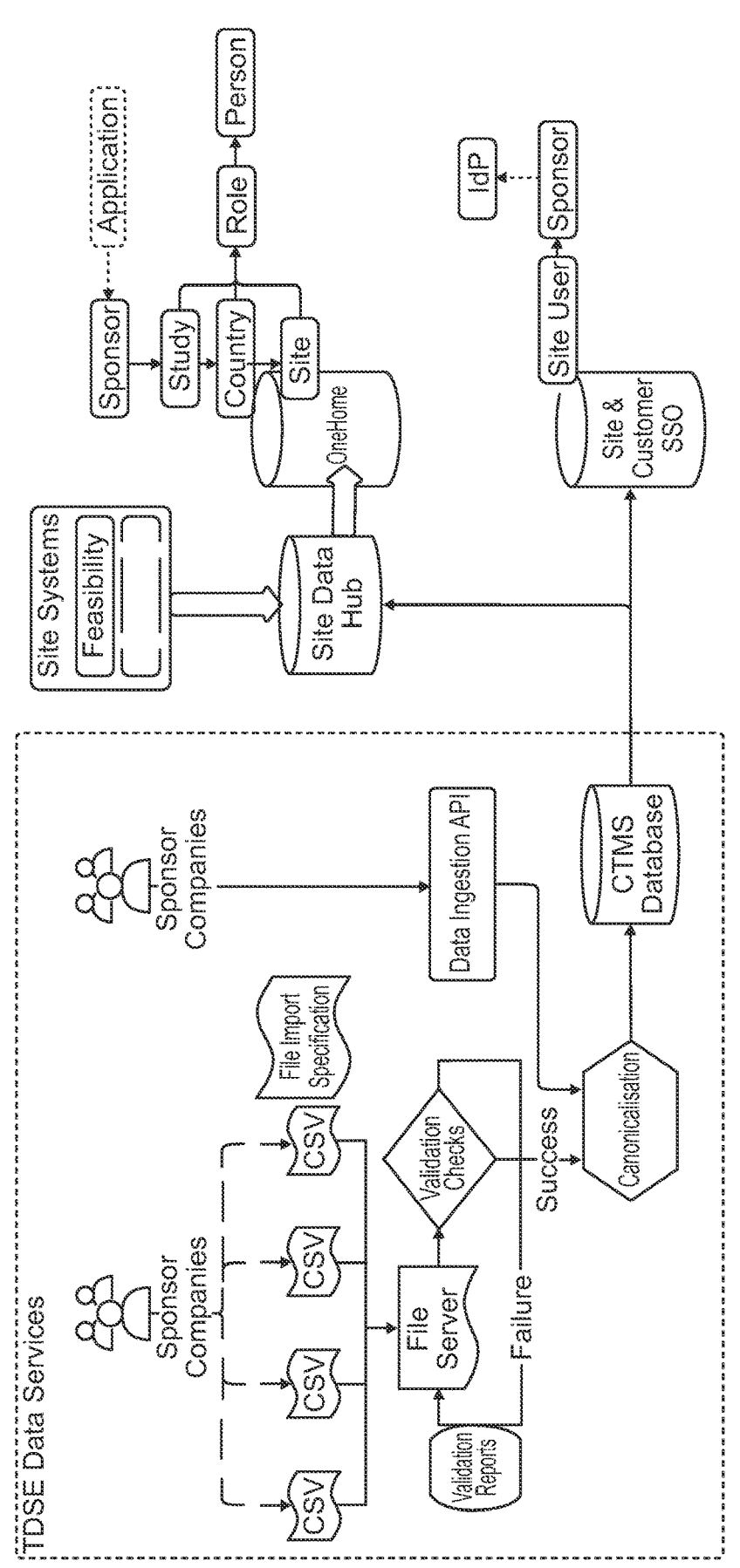
FIG. 4E illustrates a diagram of an example identify provider discovery process.

Referring to FIG. 4E, a diagram 440 illustrating an example identity provider discovery process is shown. In this example, the clinical data integration process shown in FIG. 4B is expanded to leverage the ingested clinical data for user identity provider (IdP) discovery. In doing so, information about a user (e.g., a site user) can be linked to a particular sponsor, which can then be linked to an identity provider. This information can be stored (e.g., in a site and customer SSO repository) to facilitate SSO to various applications and systems, as described herein.

Figure 5A:
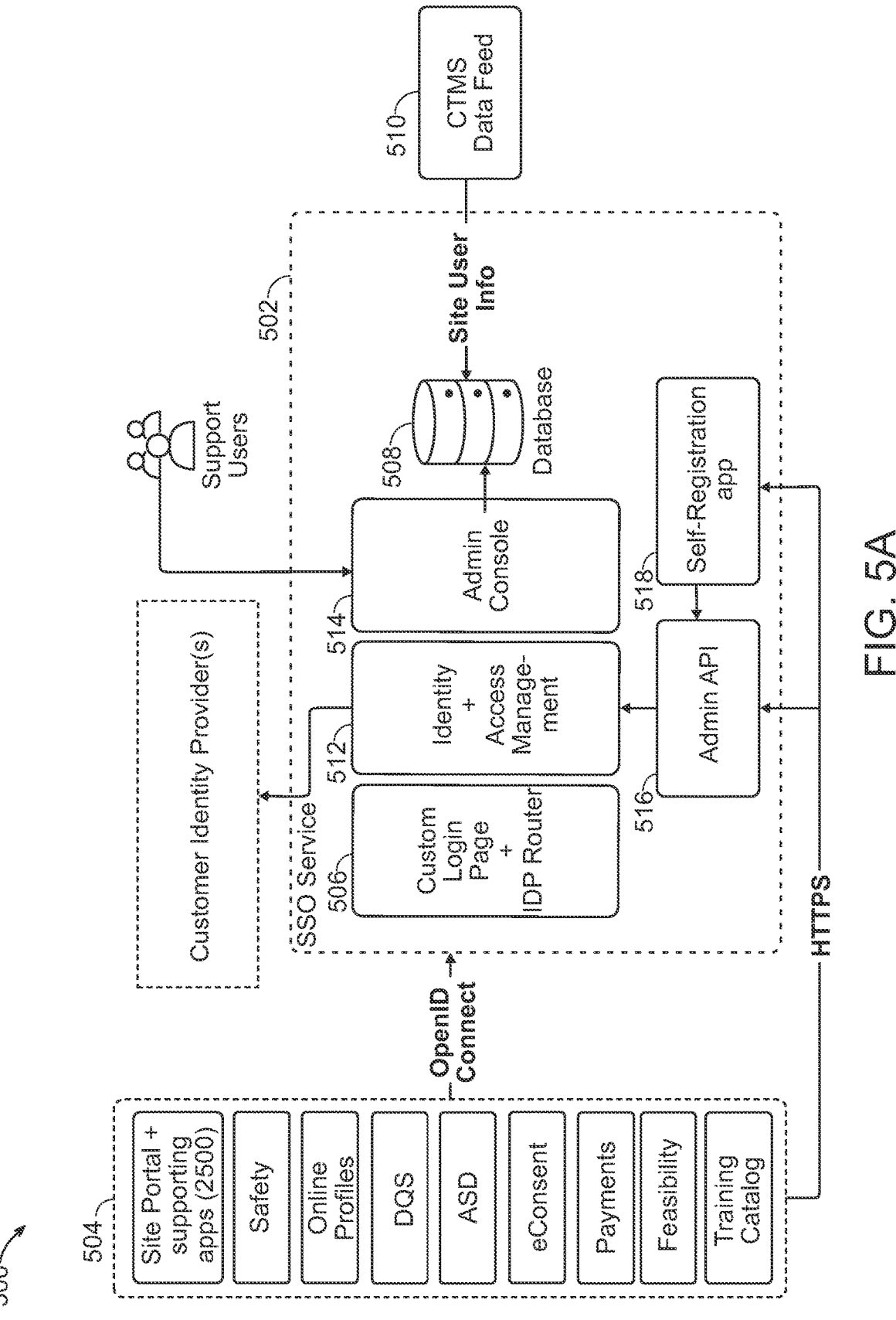
FIG. 5A illustrates a diagram of an example single sign-on (SSO) architecture.

Referring to FIG. 5A, a diagram 500 depicting an example SSO architecture of the platform 100 is shown. In this example, the SSO architecture includes an SSO service 502 that enables users to seamlessly access and move between various systems and services (e.g., site system and services 504) without the need to repeatedly input credentials. The SSO service 502 provides a customer login page and IdP router 506 that serves as an initial landing page for obtaining user credentials. Based on the user credentials, as well as clinical and/or authorization data obtained from a database 508 fed by a a clinical trial management system (CTMS) data feed 510, an identify and access management component 512 authenticates the user either internally or by interfacing with one or more customer identify providers 512. The SSO service 502 also includes an admin console 514 to facilitate management of users (e.g., password management, group management, etc.), as well as an admin API 516 and a self-registration application 518 for provisioning. Once a user is authenticated by the SSO service 502, the user is able to transition between various systems and services of the platform 100 without further credential input.

Figure 5B:
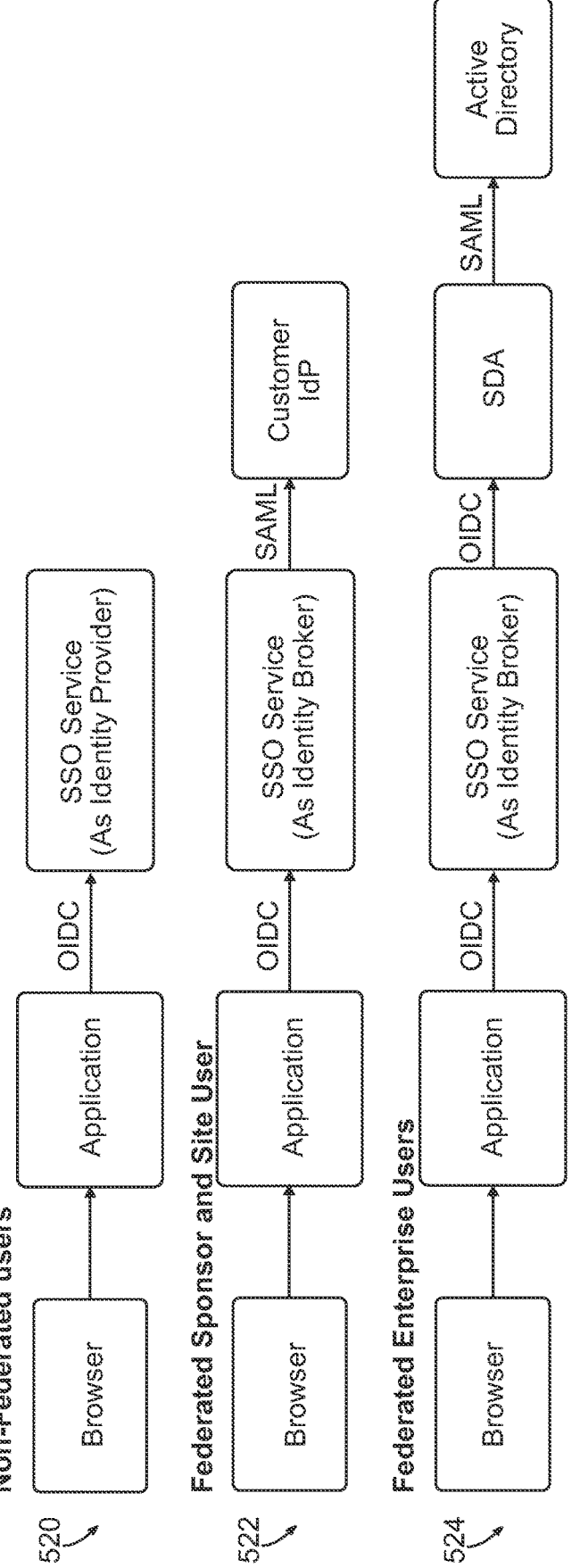
FIG. 5B illustrates example SSO authentication flows based on user type.

An important feature of the SSO service employed by the platform 100 is its ability to integrate with different user types. FIG. 5B illustrates examples of various SSO authentication flows based on user types, including non-federated users, federated sponsor and site users, and federated enterprise users. In general, a non-federated user is an external user that accesses the platform outside of an SSO-integrated sponsor domain. In some examples, a non-federated user is issued SSO credentials for the platform, and a non-federated user authentication flow 520 is used in which the user is authenticated for the various systems and services provided by the platform based on the SSO credentials. This allows the non-federated user to move between the systems and services of the platform without needing to re-enter credentials within a session.

A federated sponsor or site user is a sponsor-or site-based external user working on one or more SSO-integrated sponsor studies. To authenticate a federated sponsor or site user, a federated sponsor and site user authentication flow 522 can be used in which the user is authenticated through direct customer IdP integrations maintained by the platform. This allows the federated sponsor or site user to use their sponsor-related credentials to access and seamlessly move between the systems and services of the platform without needing to re-enter credentials within a session. In some examples, additional or alternative authentication methods can be used for federated sponsor or site users depending on from which sponsor context the user is accessing the systems and services of the platform.

A federated enterprise user is a user working within a sponsor or CRO that is integrated with the SSO service provided by the platform. To authenticate a federated enterprise user, a federated enterprise user authentication flow 524 is used in which the user is authenticated using, for example, static data authentication (SDA) that uses an active directory as a security assertion markup language (SAML) identity provider. This allows the federated user to leverage their sponsor-provided credentials to access and transition between the systems and services of the platform, where the user's email domain defines the routing.

Figure 5C:
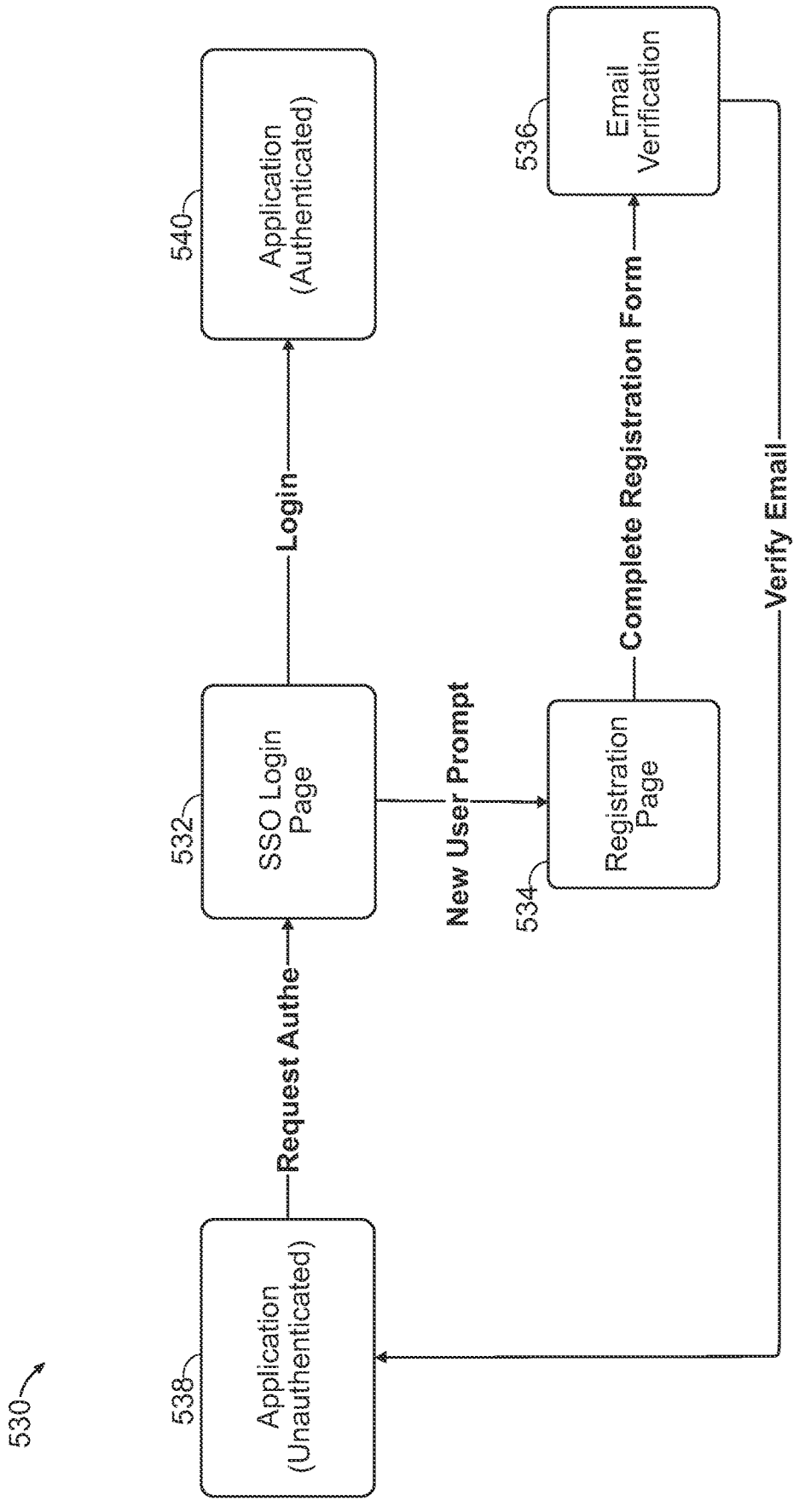
FIG. 5C illustrates an example SSO self-registration flow.

Referring to FIG. 5C, an example SSO self-registration flow 530 is shown. In this example, a user lands on the SSO login page 532 and indicates that they are a new user, leading them to the registration page 534. From here, the user completes a registration form and performs email verification 536. At this point, the user is registered, but remains unauthenticated 538 within the application. The user enters their credentials in the SSO login page 532, and is then authenticated 540 within the application. In some examples, self-registration does not guarantee access to a particular application (or system or service), but authenticates the user within the platform. This self-registration process reduces the burden on operations teams to send out provisioning request ahead of time, on users to register withing the allowable window, and on support having to solve user issues (e.g., due to invite expirations).

Figure 5D:
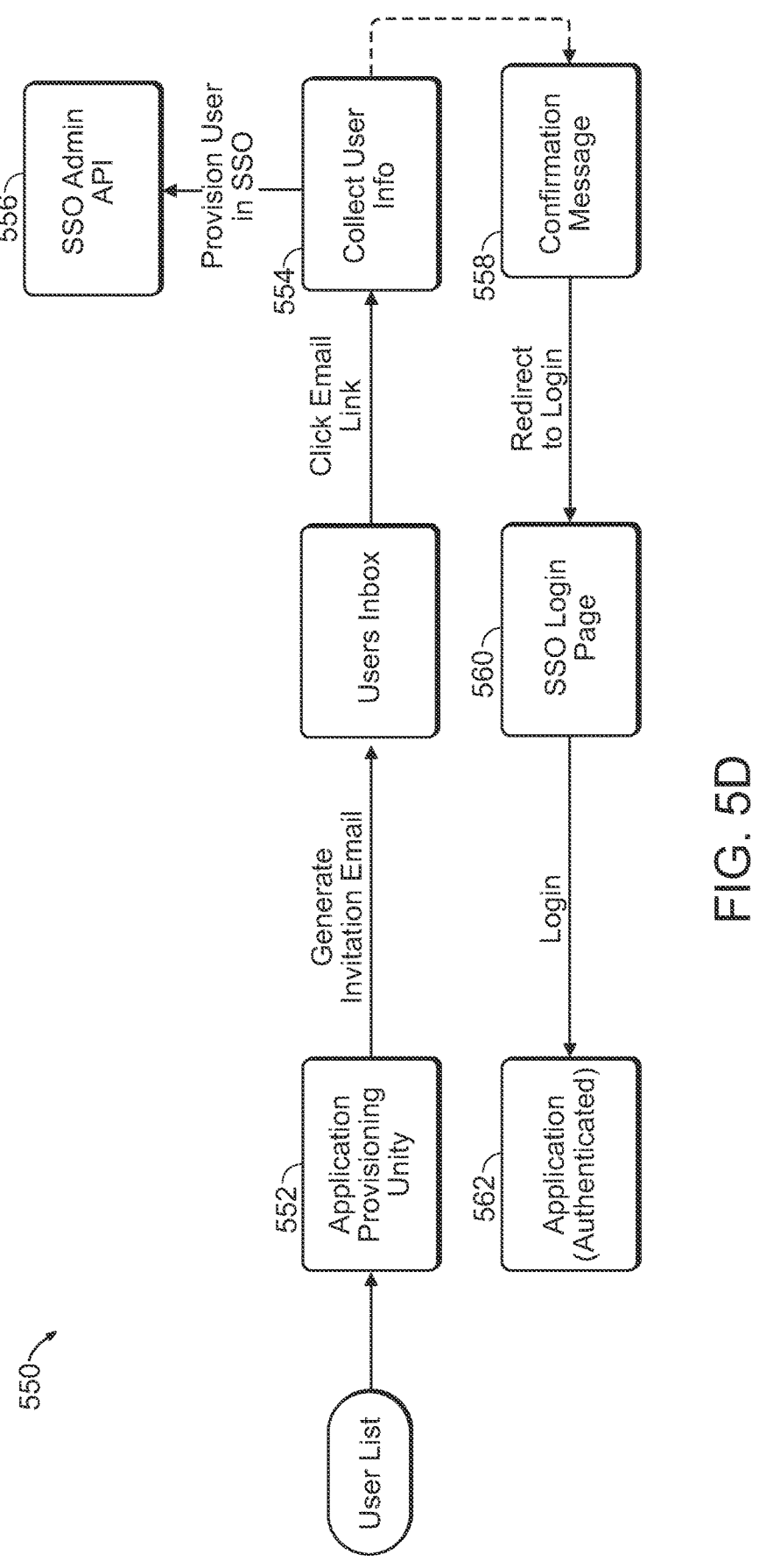
FIG. 5D illustrates an example SSO invited registration flow.

FIG. 5D illustrates an example SSO invited registration flow 550. In this example, a user list is provided to an application provisioning utility 552 that generates emails to the users in the list. A user clicks a registration link in their email and user information is collected 554. Once the user information is collected, instructions to provision the user in SSO is sent to the SSO admin API 556. A confirmation message 558 is sent upon completion of the provisioning, and the user is redirected to an SSO login page 560. From here, the user can login using their credentials, and they are authenticated 562 within applications (and/or systems or services) within the platform (though access may depend on the user's access rights).

Figure 5F:
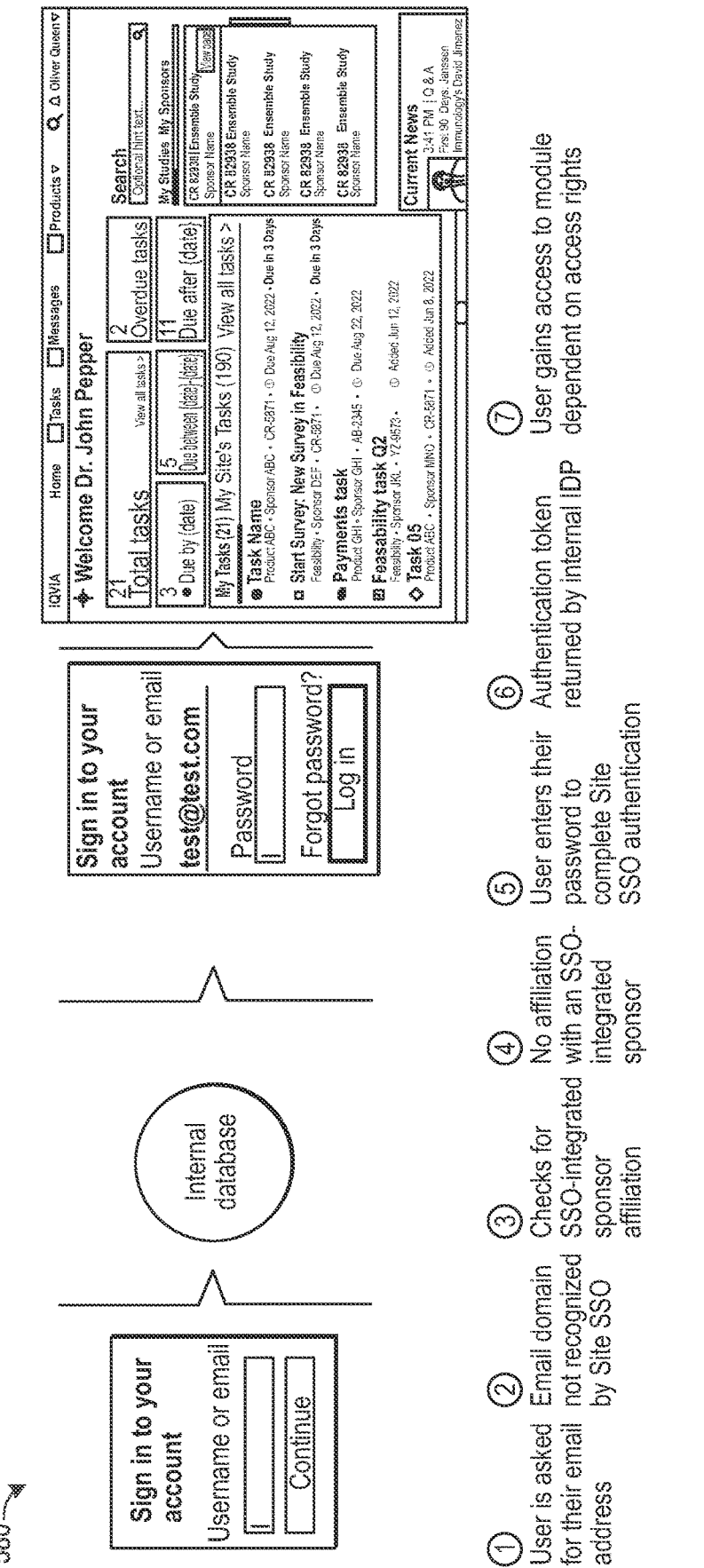
FIG. 5F illustrates an example SSO flow for a non-federated user.

FIGS. 5E-5G illustrate example SSO flows for different types of users. Referring to FIG. 5E, an example SSO flow 570 for a federated enterprise user is shown. Initially, the user accesses the login page and is asked for their email address. Next, the SSO service routes to the sponsor's IdP based on the domain in the provided email address (federated users' email addresses are from a known domain associated with an SSO- integrated enterprise). The external IdP authenticates the user, and an authentication token is returned to the SSO service by the external IdP. From here, the user is able to move seamlessly between accessible systems and services based on an access token stored in their browser session.

Referring to FIG. 5F, an example SSO flow 580 for a non-federated user is shown. Initially, the user accesses the login page and is asked for their email address. Since the non-federated user's email address is not from a domain associated with an SSO-integrated sponsor, the SSO service does not recognize the email domain. The SSO service then checks for SSO-integrated sponsor affiliation in an internal database. No affiliation with an SSO-integrated sponsor is found, and the user proceeds to enter their password to complete authentication with the SSO service. An authentication token is returned by an internal IdP and stored in the user's browser session, thereby enabling them to gain access to systems and services based on their access rights.

Referring to FIG. 5G, an example SSO flow 590 for a federated site user is shown. In this example, the user accesses the login page and is asked for their email address. The SSO service checks whether the domain of the provided email address is associated with an internal site IdP, and/or whether the domain is affiliated with an SSO- integrated sponsor. Based on these checks, the SSO service provides the user with an option to sign in with their platform account and/or their sponsor-affiliated account. Based on the selected option, the SSO service authenticates the user using either an internal or external IdP. An authentication token is returned from the respective IdP and stored in the user's browser session to allow them access to systems and services based on their access rights.

Figure 6A:
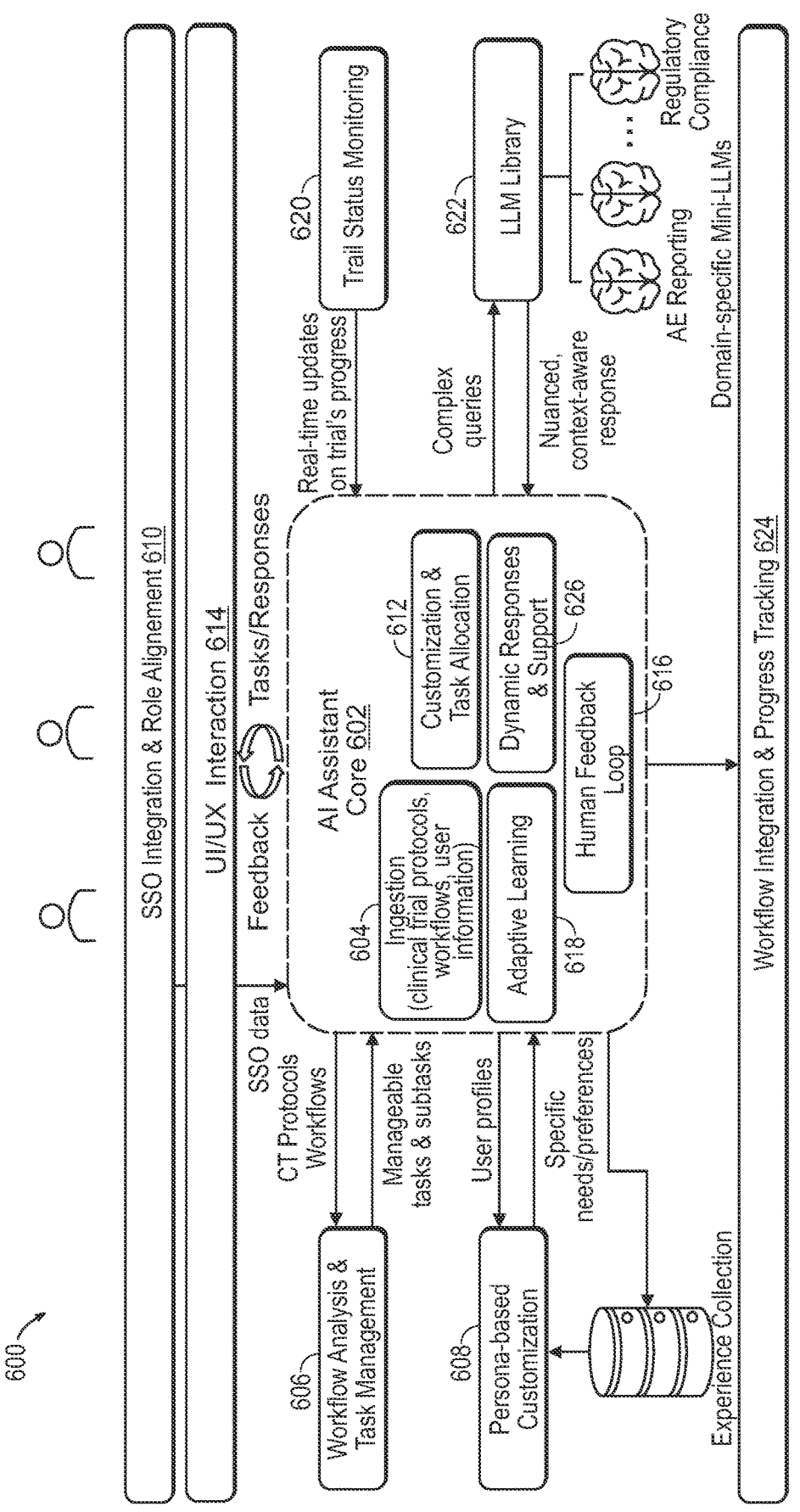
FIG. 6A illustrates a diagram of an example data flow for an AI assistant within the platform.

Referring to FIG. 6A, a diagram 600 depicting an example data flow for an AI assistant within the platform is shown. In this example, the AI assistant includes an AI assistant core 602 having an ingestion component 604 that ingests data including, but not limited to, clinical trial protocols, workflows, and user information. This data can be sourced from, for example, trial databases, user inputs, and integrated systems. A workflow analysis and task management component 606 leverages AI algorithms to analyze the trial protocols and workflows to break them down into individual tasks and subtasks. A persona-based customization component 608 processes user data (e.g., roles, preferences, past interactions, and other user information), and feeds back specific needs and/or preferences to the AI assistant core 602. In some examples, the AI assistant (e.g., the AI assistant core 602) can process and analyze data in real-time or near-real-time to provide real-time or near-real-time insights or alerts to a user.

An SSO integration and role alignment component 610 uses SSO data to identify and verify user roles and access rights. A customization and task allocation component 612 of the AI assistant core 602 uses the information from the persona-based customization component 608 and the SSO integration and role alignment component 610 to generate customized task lists and interfaces for different user personas by allocating tasks to users based on their roles, expertise, and current workflow needs.

Users interact 614 with the AI assistant by executing tasks and providing feedback on the assistant's suggestions and functionality. This feedback is captured by the human feedback loop component 616. An adaptive learning component 618 of the AI assistant core 602 analyzes the feedback to learn and adapt. This enables the AI assistant to continuously updates task prioritization and user interaction strategies.

A trial status monitoring and model adjustment component 620 keeps track of the overall progress and phase of the trial. Depending on the trial status, the component informs the AI assistant core 602 to adjust its operational models and tools.

For complex queries, the AI assistant core 602 accesses a large language model (LLM) library 622 to select appropriate models for language understanding and response generation. Domain-specific LLMs (e.g., mini-LLMs) are activated for specialized tasks providing targeted assistance.

The AI assistant integrates its functionalities with the clinical trial's workflow using a workflow integration and progress tracking component 624. This component monitors the progress of tasks and the trial, providing updates and insights to users. As the trial progresses through different stages, AI assistant dynamically adjusts its support, tools and models via the dynamic response and support component 626. In this way, the AI assistant ensures that users receive relevant assistance and information at each stage of the trial.

Given the sensitivity of clinical trial data, in some examples, the AI assistant is configured to ensure compliance with regulatory standards (e.g., by masking PHI/PII) and provides data security protections (e.g., through encryption and other means).

Figure 6B:
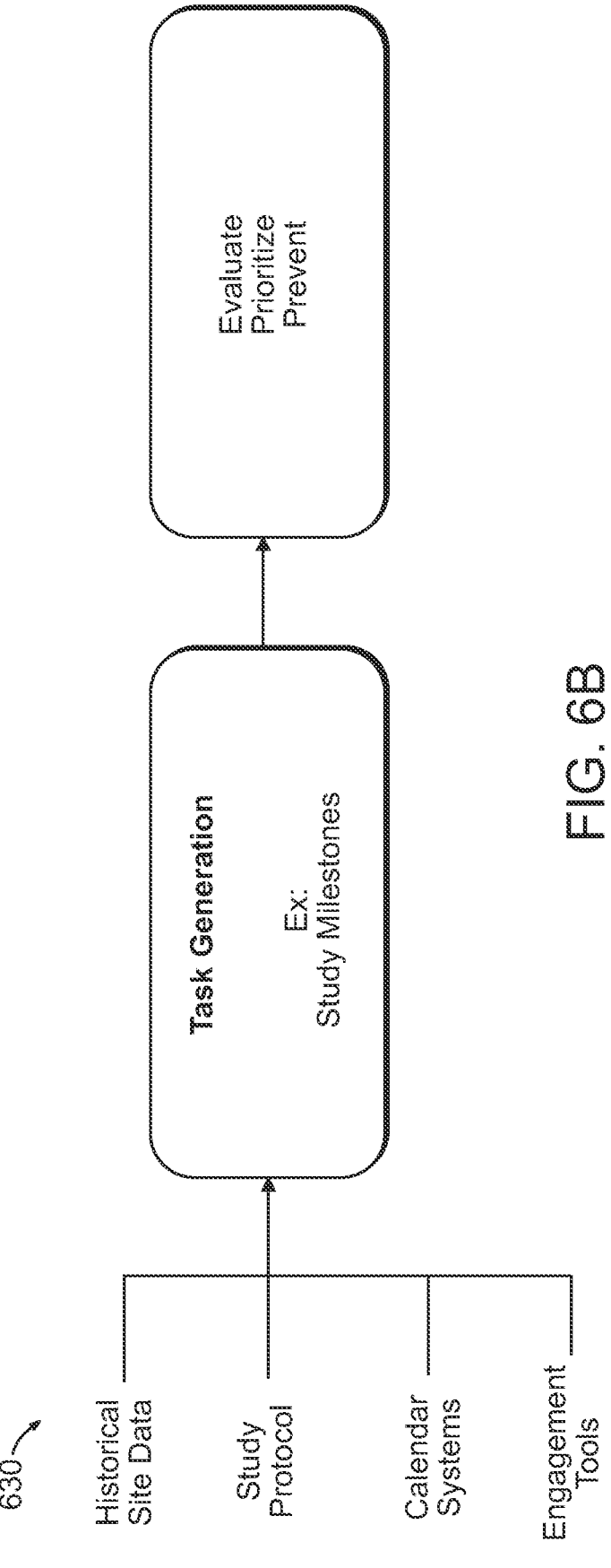
FIG. 6B illustrates an example of AI task flow prioritization and management.

Referring to FIG. 6B, an example flow 630 for AI task flow prioritization and management is shown. Such a flow can be utilized by the AI assistant described in FIG. 6A. In this example, historical site data, study protocols, calendar systems, and engagement tools are provided to a task generation component, which then evaluates these data and tools to prioritize and manage tasks. In some examples, the task generation component leverages predictive AI algorithms that learn from previous trial data to predict and prioritize tasks. In some examples, NLP/LLM are used for understanding and automating complex task descriptions from study protocols. The task generation component can use predictive analytics to anticipate potential bottlenecks in the trial process and suggest proactive measures. In some examples, the task generation component suggests the next best actions for users, integrate with calendar systems to align tasks with users' schedules, and pushes notifications to preferred devices, enhancing the overall efficiency of clinical trial management.

Figure 6C:
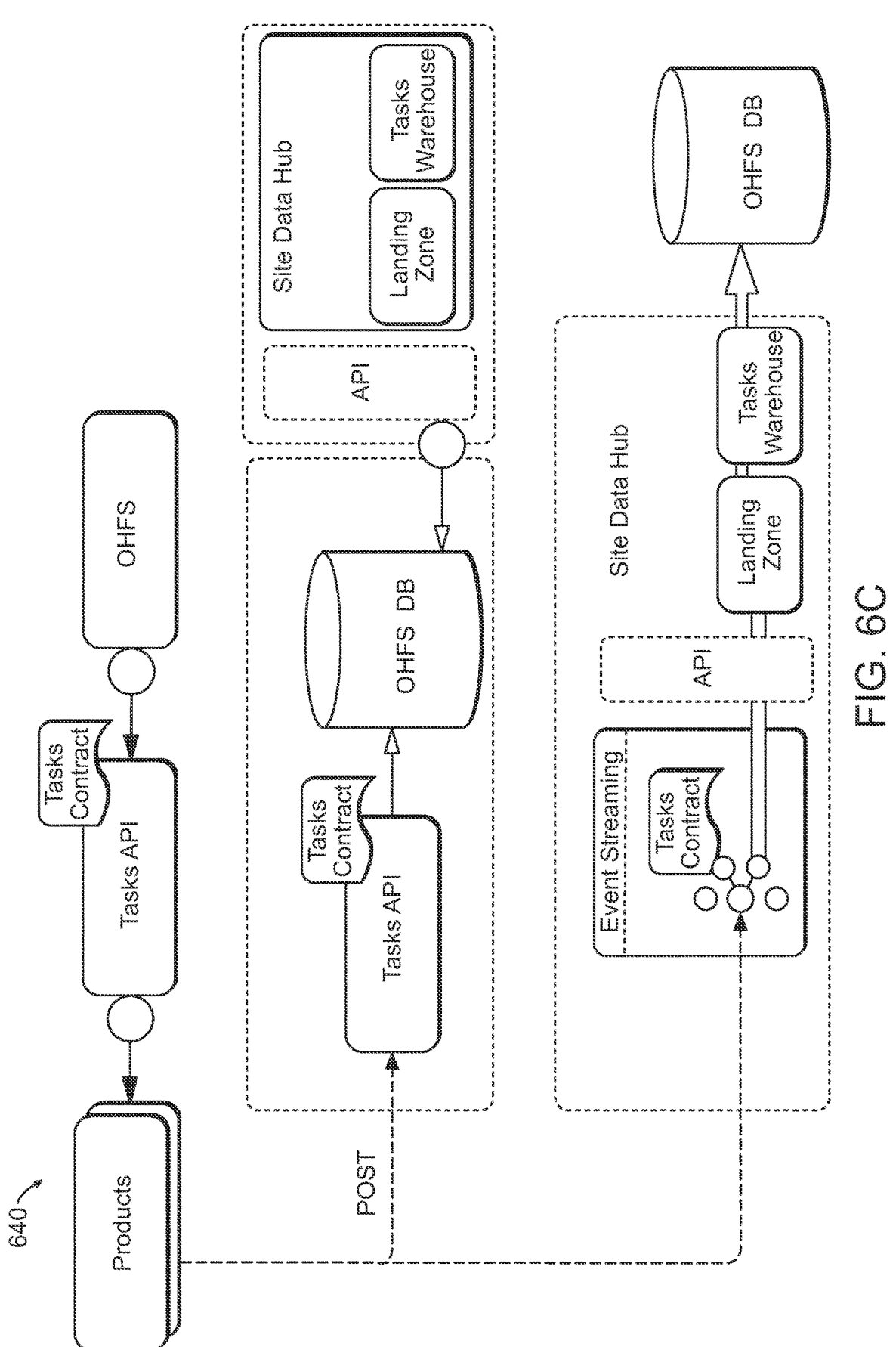
FIG. 6C illustrates an example architecture for generation of tasks.

FIG. 6C illustrates an example architecture 640 for generation of tasks within the platform. In this example, the platform publishes a standardized tasks contract, and participating systems and services implement a task API based on the API contract. The platform then uses a configurable framework to pull, aggregate, and render tasks from the systems and services at runtime. In some examples, the rendering of tasks can leverage AI and other tools, as described herein. To improve scalability, a push model can be used in some examples. Alternatively, or in addition, the platform can provide real-time or near-real-time streaming capabilities for systems and services to publish tasks to the platform.

Figure 7:
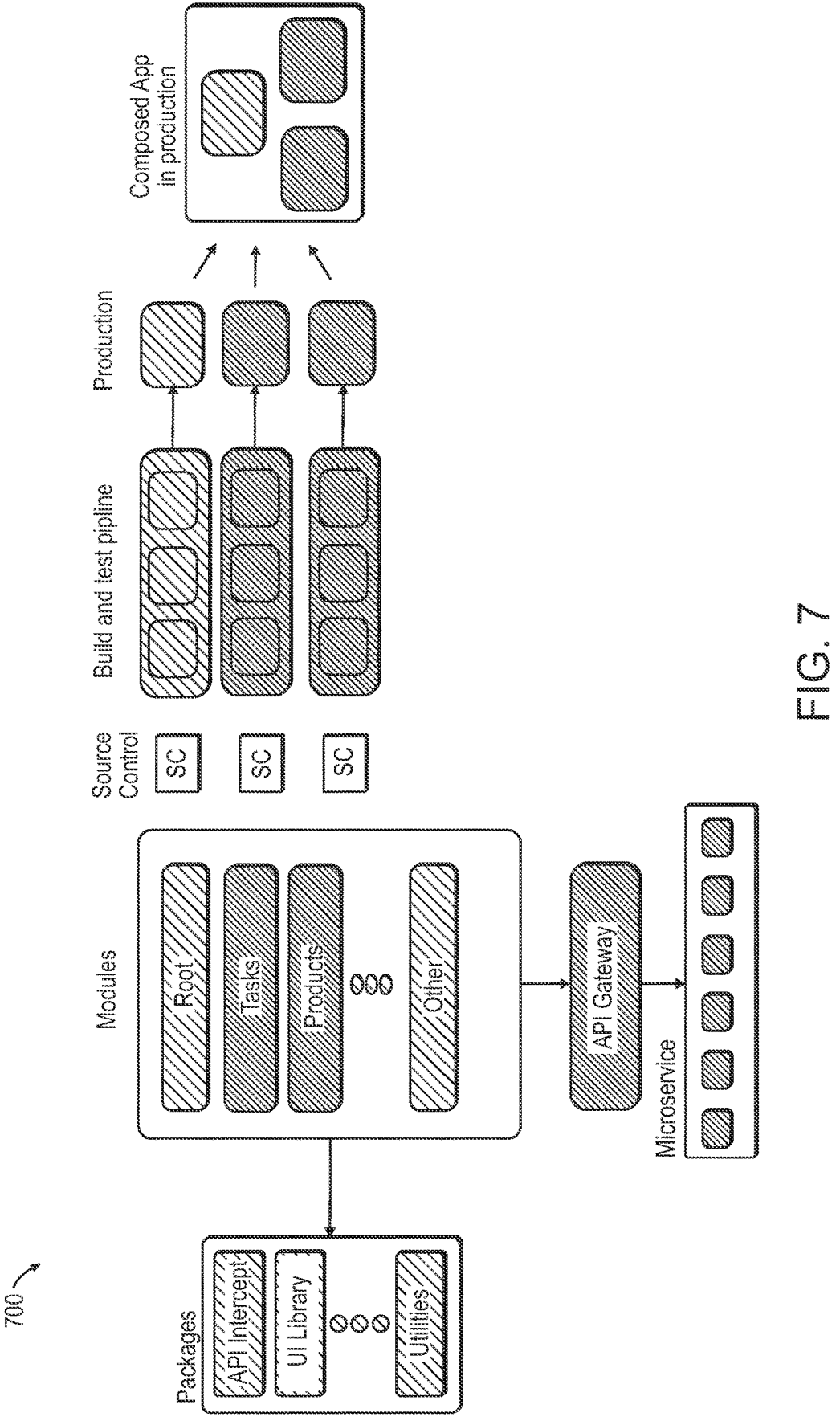
FIG. 7 illustrates a diagram of an example micro frontend.

Referring to FIG. 7, an example micro frontend 700 employed by the platform is shown. The micro frontend 700 has a resilient, maintainable, and scalable design that helps develop modules in isolation by separate teams, making it loosely coupled. The micro frontend 700 follows a module-based deployment, as opposed to monolithic approach, which mitigates the risk of interfering with the whole application and reduces the amount of effort needed for regression. The micro frontend 700 is also tech-stack agnostic, thereby enabling compatibility with a wide range of frontend applications.

Figure 8:
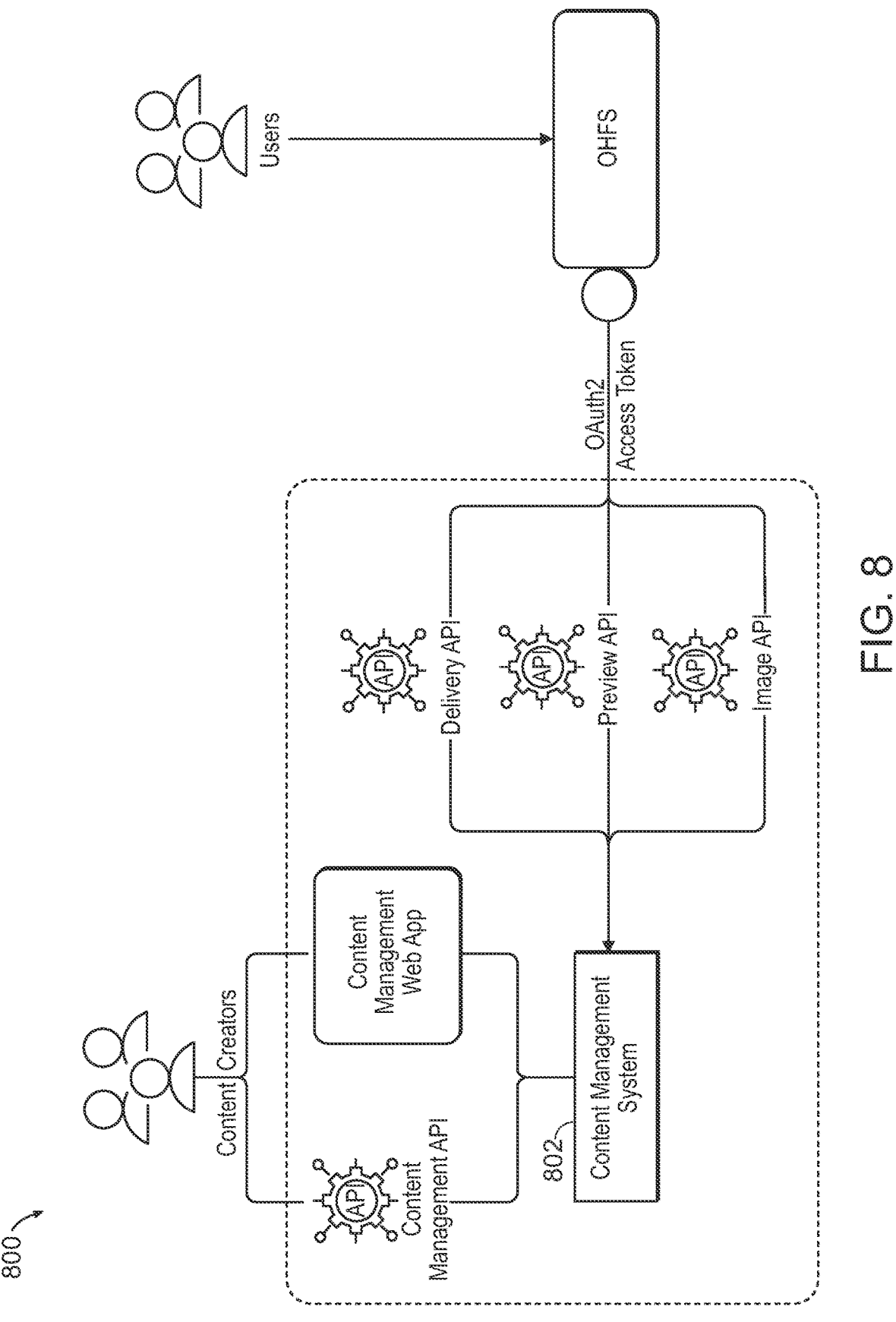
FIG. 8 illustrates an example content architecture.

FIG. 8 illustrates an example content architecture 800 used by the platform. In this example, a content management system 802 is leveraged to create, manage, and distribute content to the platform. The architecture 800 utilizes an API first design in which every content object is created with an API endpoint, which provides the ability to isolate content (e.g., sponsor content). In some examples, the architecture 800 can be used to provide role-based security in which access to creation, management, and/or distribution of content is dictated by role. The architecture 800 can also provide features such as content tagging, content previewing (e.g., via a content preview API), a content approval workflow, and static content handling.

Figure 9:
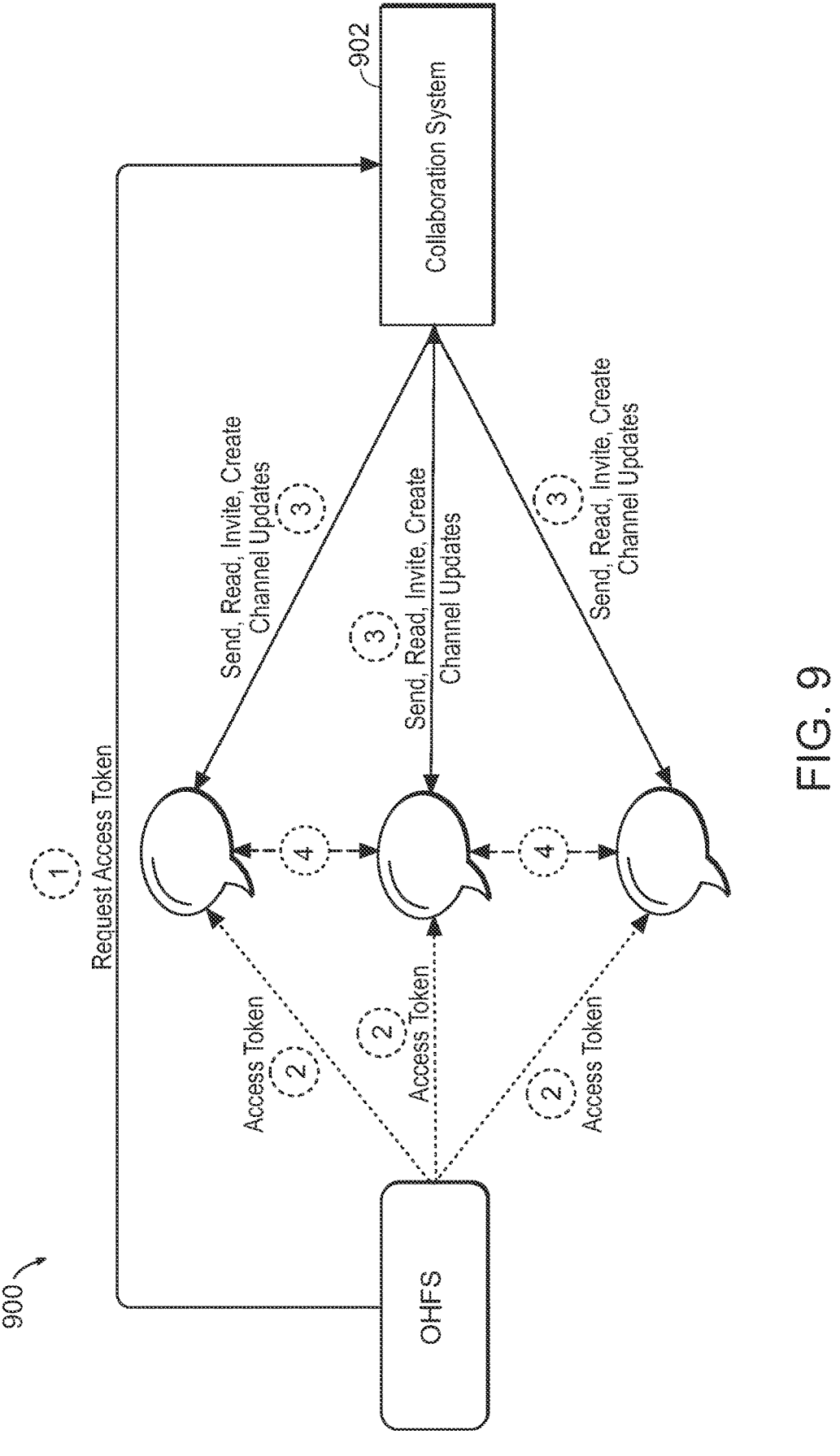
FIG. 9 illustrates an example conversation flow.

Referring to FIG. 9, an example conversation flow 900 is shown. In this example, the platform requests an access token from a collaboration system 902 to authenticate and provide access to the services by one or more users. In some examples, backend authentication is done using API keys, and client-side authentication is done using access tokens (e.g., JSON web tokens). Once received, the access tokens are provided to users, which enables the users send, receive, invite, and/or create chats, including 1-1 chats and group chats. In some examples, the platform can suggest chat contacts or chat groups based on, for example, analysis of study data and/or chat history, which can include AI/LLM analysis. The platform can also analyze chats to identify tasks, which can be fed into the task management systems described herein. This allows the platform to promote secure and effective communication with the right contacts. In some examples, chat transcripts can be stored in an electronic trial master file.

Figure 10:
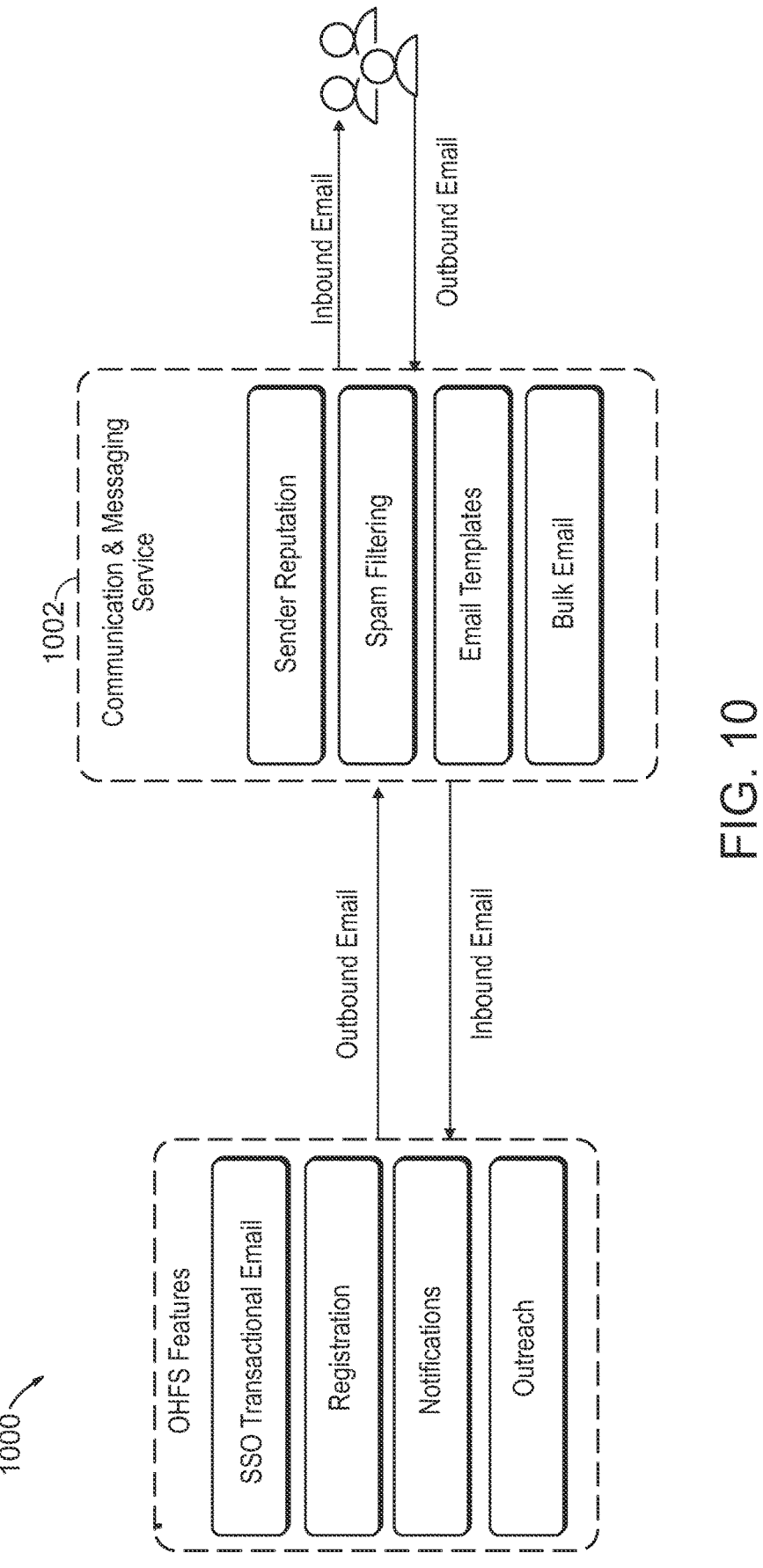
FIG. 10 illustrates an example email architecture.

FIG. 10 illustrates an example architecture 1000 for email within the platform. In this example, the platform sends outbound emails, such as SSO transaction emails, registration emails, notification emails, and other outreach emails to a communication and messaging service 1002 for delivery to intended recipients. In some examples, backend authentication can be done using an API key and secret, thereby enabling secure, reliable transactional email delivery and tracking.

Figure 11:
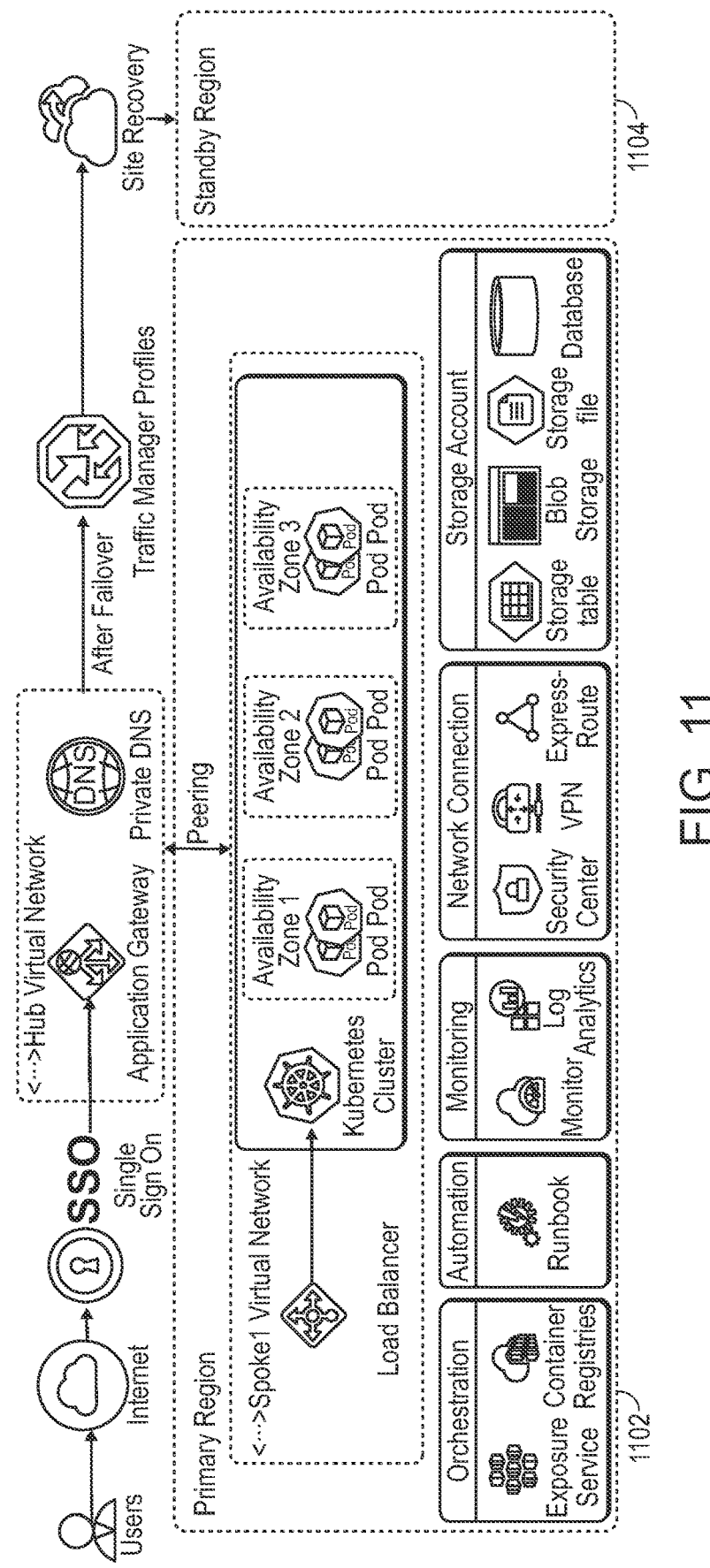
FIG. 11 illustrates an example clinical trial management infrastructure.

Referring to FIG. 11, an example clinical trial management infrastructure 1100 is shown. In general, the infrastructure 1100 includes various components for implementing the platform architectures described with reference to FIGS. 1-3. The infrastructure 1100 is a highly available, load balanced web infrastructure with scalable storage and passive disaster recovery (e.g., through scheduled backup from a primary region 1102 to a standby region 1104). The infrastructure 1100 includes components to provide automated containerized environments, automatic scaling up or down, proactive monitoring, and multi-cloud consideration.

FIG. 12 is a flowchart of an example process 1200 for clinical trial management. For convenience, the process 1200 will be described as being performed by a system of one or more computers, located in one or more locations, and programmed appropriately in accordance with this specification. For example, a clinical trial management platform, e.g., the clinical trial management platform 100 FIG. 1, appropriately programmed, can perform the process 1200.

Operations of the process 1200 include ingesting, by a clinical trial management platform, data from multiple clinical trial site systems associated with multiple clinical trials (1202). In some examples, the multiple clinical trial software services include one or more of: a clinical trial investigator site portal, a clinical trial safety module, a clinical trial consent module, a clinical trial financial module. In some examples, at least one of the multiple clinical trial software services is provided by a different vendor than the other clinical trial software services. In some examples, ingesting the data includes ingesting one or more of site activation data, site engagement data, training data, feasibility data, safety data, profile data, or payment data. In some examples, ingesting the data includes masking personally identifiable information (PII) or personal health information (PHI) in the ingested data. In some examples, ingesting the data includes standardizing a format of the ingested data from different clinical trial site systems In some examples, the ingested data is indexed.

Responsive to authentication of user credentials of a user, the user is provided with access to the clinical trial management platform (1204). In some examples, the user credentials include user credentials for a federated enterprise system, and the operations include receiving an indication of authentication of the user credentials from the federated enterprise system. A particular one of the clinical trials associated with the user is identified based on the user credentials (1206). In some examples, identifying the clinical trial software services to which to provide access is based on a role of the user in the clinical trial.

The user is provided with access to multiple clinical trial software services through the clinical trial management platform based on the authenticated user credentials (1208). The multiple clinical trial software services include software services for the particular clinical trial associated with the user. In some examples, providing the user access to the multiple clinical trial software services includes allowing the user to access the multiple clinical trial software services without re-entering the user credentials.

Based on the ingested data for the particular clinical trial associated with the user, presenting to the user, through the clinical trial management platform, a user-specific task list for user tasks related to the particular clinical trial (1210). In some examples, the ingested data is processed using a predictive model to identify or schedule the user tasks for the user-specific task list. In some examples, the ingested data is processed using a predictive model based on a context of the data to identify or schedule one or more of the user tasks or to provide a notification to the user In some examples, data indicative of progress of the particular clinical trial is processed using the predictive model to suggest a next task for the user. In some examples, operation of the predictive model is adjusted based on user interaction with the clinical trial management platform. In some examples, operations of the process 1200 include processing the ingested data using a predictive model, and automating one or more of the user tasks based on the processed ingested data and based on a role of the user.

Through the clinical trial management platform, a communication link is established between the user and another user associated with the particular clinical trial, the communication link enabling direct, real-time messaging via the clinical trial management platform between the user and the other user (1212). In some examples, establishing a communication link includes establishing a chat session. In some examples, establishing the chat session includes establishing a chat session among multiple users associated with the particular clinical trial.

In some examples, operations of the process 1200 further include presenting, to a user, a single sign-on interface for the clinical trial management platform, receiving the user credentials through the single sign-on interface, and authenticating the received user credentials.

In some examples, operations of the process 1200 further include processing the ingested data using a predictive model based on the role of the user to provide a user-specific recommendation or alert.

In some examples, ingesting the data includes merging clinical and product authorization metadata. In some examples, the particular clinical trial associated with the user is identified based on the merged clinical and product authorization metadata. In some examples, the clinical trial software services to which to provide access are identified based on the merged clinical and product authorization metadata.

In some examples, operations of the process 1200 include facilitating communication using a generative artificial intelligence (AI) tool. In some examples, facilitating communication includes translating or summarizing content and providing the translated or summarized content to the user. In some examples, facilitating communication includes generating a suggested communication using the generative AI tool. In some examples, a large language model for the generative AI tool is automatically selected based on metadata associated with the user.

To provide such functionality, the platform (e.g., the platform 100) may include, be in communication with, associated with, etc., one or more types of computation devices that include one or more components (e.g., processors, memories, etc.). Memory stores program instructions and data used by the processor of the intrusion detection panel. The memory may be a suitable combination of random access memory and read- only memory, and may host suitable program instructions (e.g. firmware or operating software), and configuration and operating data and may be organized as a file system or otherwise. The program instructions stored in the memory of the panel may store software components allowing network communications and establishment of connections to the data network.

Program instructions stored in the memory, along with configuration data may control overall operation of the system. Server computer systems include one or more processing devices (e.g., microprocessors), a network interface and a memory (all not illustrated). Server computer systems may physically take the form of a rack mounted card and may be in communication with one or more operator terminals (not shown).

All or part of the processes described herein and their various modifications (hereinafter referred to as "the processes") can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing the processes can be performed by one or more programmable processors executing one or more computer programs to perform the functions of the calibration process. All or part of the processes can be implemented as, special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks.

Tangible, physical hardware storage devices that are suitable for embodying computer program instructions and data include all forms of non-volatile storage, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory.

In addition, the logic flows depicted in the figures do not require the particular order shown, or sequential order, to achieve desirable results. In addition, other actions may be provided, or actions may be eliminated, from the described flows, and other components may be added to, or removed from, the described systems. Likewise, actions depicted in the figures may be performed by different entities or consolidated.

This specification uses the term "configured to" in connection with systems, apparatus, and computer program components. That a system of one or more computers is configured to perform particular operations or actions means that the system has installed on it software, firmware, hardware, or a combination of them that in operation cause the system to perform the operations or actions. That one or more computer programs is configured to perform particular operations or actions means that the one or more programs include instructions that, when executed by data processing apparatus, cause the apparatus to perform the operations or actions. That special-purpose logic circuitry is configured to perform particular operations or actions means that the circuitry has electronic logic that performs the operations or actions.

The subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some implementations, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

Elements of different embodiments described herein may be combined to form other embodiments not specifically set forth above. Elements may be left out of the processes, computer programs, Web pages, etc. described herein without adversely affecting their operation. Furthermore, various separate elements may be combined into one or more individual elements to perform the functions described herein.

Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method comprising:

ingesting, by a clinical trial management platform, data from multiple clinical trial site systems associated with multiple clinical trials;

responsive to authentication of user credentials of a user, providing the user with access to the clinical trial management platform;

based on the user credentials, identifying a particular one of the clinical trials associated with the user;

through the clinical trial management platform, providing the user with access to multiple clinical trial software services based on the authenticated user credentials, wherein the multiple clinical trial software services comprise software services for the particular clinical trial associated with the user;

identifying, by an artificial intelligence (AI) assistant, a user-specific task list for user tasks related to the particular clinical trial by processing, with a first predictive model and to generate the user-specific task list, a subset of the data from the multiple clinical trial site systems associated with the multiple clinical trials, wherein the subset of the data is associated with the particular clinical trial associated with the user with a first predictive model to generate the user-specific task list;

prioritizing, by the AI assistant, the user tasks of the user-specific task list by processing the user-specific task list, a user persona associated with the user, and a current status of the particular clinical trial with a second predictive model to generate a prioritized user-specific task list;

presenting to the user, through the clinical trial management platform, the prioritized user-specific task list; and through the clinical trial management platform, establishing a communication link between the user and another user associated with the particular clinical trial, the communication link enabling direct, real-time messaging via the clinical trial management platform between the user and the other user.

2. The method of claim 1, comprising:

user credentials received through a single sign-on interface for the clinical trial management platform.

3. The method of claim 1, wherein the user credentials comprise user credentials for a federated enterprise system, and wherein the method comprises receiving an indication of authentication of the user credentials from the federated enterprise system.

4. The method of claim 1, wherein providing the user access to the multiple clinical trial software services comprises allowing the user to access the multiple clinical trial software services without re-entering the user credentials.

5. The method of claim 1, wherein at least one of the multiple clinical trial software services is provided by a different vendor than the other clinical trial software services.

6. The method of claim 1, wherein the multiple clinical trial software services comprise a clinical trial investigator site portal, a clinical trial safety module, a clinical trial consent module, and a clinical trial financial module.

7. The method of claim 1, comprising identifying the clinical trial software services to which to provide access based on a role of the user in the clinical trial.

8. The method of claim 7, comprising using a predictive model, processing the subset of the ingested data based on the role of the user to provide a user-specific recommendation.

9. The method of claim 1, wherein ingesting the data comprises ingesting site activation data, site engagement data, training data, feasibility data, safety data, profile data, and payment data.

10. The method of claim 1, comprising indexing the ingested data.

11. The method of claim 1, comprising masking personally identifiable information (PII) and personal health information (PHI) in the ingested data.

12. The method of claim 1, comprising standardizing a format of the ingested data from different clinical trial site systems.

13. The method of claim 1, wherein ingesting the data comprises merging clinical and product authorization metadata.

14. The method of claim 13, comprising identifying the particular clinical trial associated with the user based on the merged clinical and product authorization metadata.

15. The method of claim 13, comprising identifying the clinical trial software services to which to provide access based on the merged clinical and product authorization metadata.

16. The method of claim 1, comprising processing data indicative of progress of the particular clinical trial using the first predictive model to suggest a next task for the user.

17. The method of claim 16, comprising adjusting operation of the first predictive model based on user interaction with the clinical trial management platform.

18. The method of claim 1, comprising automating one or more of the user tasks based on the subset of the ingested data processed using a predictive model and based on a role of the user.

19. The method of claim 1, comprising using a predictive model, processing the subset of the ingested data based on a context of the data to schedule one or more of the user tasks.

20. The method of claim 1, wherein establishing a communication link comprises establishing a chat session.

21. The method of claim 20, wherein establishing the chat session comprises establishing a chat session among multiple users associated with the particular clinical trial.

22. The method of claim 1, comprising facilitating communication using a generative artificial intelligence (AI) tool.

23. The method of claim 22, comprising automatically selecting, based on metadata associated with the user, a large language model for the generative AI tool.

24. The method of claim 22, wherein facilitating communication comprises translating and summarizing content and providing the translated and summarized content to the user.

25. The method of claim 22, wherein facilitating communication comprises generating a suggested communication using the generative AI tool.

26. A system comprising:

one or more processors; and one or more computer-readable storage devices storing instructions executable by the one or more processors to perform operations comprising:

ingesting, by the system, data from multiple clinical trial site systems associated with multiple clinical trials;

responsive to authentication of user credentials of a user, providing the user with access to the system;

based on the user credentials, identifying a particular one of the clinical trials associated with the user;

through the system, providing the user with access to multiple clinical trial software services based on the authenticated user credentials, wherein the multiple clinical trial software services comprise software services for the particular clinical trial associated with the user;

identifying, by an artificial intelligence (AI) assistant, a user-specific task list for user tasks related to the particular clinical trial by processing, with a first predictive model and to generate the user-specific task list, a subset of the data from the multiple clinical trial site systems associated with the multiple clinical trials, wherein the subset of the data is associated with the particular clinical trial associated with the user with a first predictive model to generate the user-specific task list;

prioritizing, by the AI assistant, the user tasks of the user-specific task list by processing the user-specific task list, a user persona associated with the user, and a current status of the particular clinical trial with a second predictive model to generate a prioritized user-specific task list;

presenting to the user, through the system, the prioritized user-specific task list; and through the system, establishing a communication link between the user and another user associated with the particular clinical trial, the communication link enabling direct, real-time messaging via the system between the user and the other user.

27. A non-transitory computer-readable storage medium storing instructions executable by one or more processors to perform operations comprising:

ingesting, by a clinical trial management platform, data from multiple clinical trial site systems associated with multiple clinical trials;

responsive to authentication of user credentials of a user, providing the user with access to the clinical trial management platform;

based on the user credentials, identifying a particular one of the clinical trials associated with the user;

through the clinical trial management platform, providing the user with access to multiple clinical trial software services based on the authenticated user credentials, wherein the multiple clinical trial software services comprise software services for the particular clinical trial associated with the user;

identifying, by an artificial intelligence (AI) assistant, a user-specific task list for user tasks related to the particular clinical trial by processing, with a first predictive model and to generate the user-specific task list, a subset of the data from the multiple clinical trial site systems associated with the multiple clinical trials, wherein the subset of the data is associated with the particular clinical trial associated with the user with a first predictive model to generate the user-specific task list;

prioritizing, by the AI assistant, the user tasks of the user-specific task list by processing the user-specific task list, a user persona associated with the user, and a current status of the particular clinical trial with a second predictive model to generate a prioritized user-specific task list;

presenting to the user, through the system, the prioritized user-specific task list; and through the clinical trial management platform, establishing a communication link between the user and another user associated with the particular clinical trial, the communication link enabling direct, real-time messaging via the clinical trial management platform between the user and the other user.

* * * * *